(12) United States Patent
Lee

(10) Patent No.: US 8,920,423 B2
(45) Date of Patent: Dec. 30, 2014

(54) BONE HARVESTING DEVICE

(76) Inventor: Benjamino Kah Hung Lee, North Point (HK)

( * ) Notice: Subject to any disclaimer, the term of this patent is extended or adjusted under 35 U.S.C. 154(b) by 48 days.

(21) Appl. No.: 13/272,514

(22) Filed: Oct. 13, 2011

(65) Prior Publication Data

US 2012/0191096 A1    Jul. 26, 2012

(30) Foreign Application Priority Data

Jan. 21, 2011    (GB) .................................. 1101160.8

(51) Int. Cl.
| A61B 17/00 | (2006.01) |
| A61C 8/00 | (2006.01) |
| A61B 17/16 | (2006.01) |
| A61F 2/44 | (2006.01) |

(52) U.S. Cl.
CPC ........... *A61C 8/0089* (2013.01); *A61B 17/1635* (2013.01); *A61C 8/0092* (2013.01); *A61F 2002/4445* (2013.01)
USPC .......................................................... 606/80

(58) Field of Classification Search
USPC ......... 606/79, 80, 82, 176, 180; 433/165, 166
See application file for complete search history.

(56) References Cited

U.S. PATENT DOCUMENTS

| 3,913,566 | A |   | 10/1975 | Lacey |   |
| 4,941,466 | A | * | 7/1990 | Romano | ........................ 606/80 |
| 6,309,394 | B1 | * | 10/2001 | Staehlin et al. | .................. 606/79 |
| 2006/0111724 | A1 |   | 5/2006 | Yeung Wai Ping |   |
| 2006/0241629 | A1 |   | 10/2006 | Krebs et al. |   |
| 2007/0118050 | A1 |   | 5/2007 | Accordino |   |

FOREIGN PATENT DOCUMENTS

| CN | 2216815 Y | 1/1996 |
| CN | 200970259 Y | 11/2007 |
| CN | 201227308 Y | 4/2009 |
| EP | 1175870 A | 1/2002 |
| EP | 1849418 A | 10/2007 |
| SU | 1669434 A1 | 8/1991 |
| WO | WO2010/046426 A1 | 4/2010 |

OTHER PUBLICATIONS

Freilich, Marshall M., et al, In-Office Iliac Crest Bone Harvesting for Peri-Implant Jaw Reconstruction, JCDA, Jul./Aug. 2006, vol. 72, No. 6, pp. 543-547.

(Continued)

*Primary Examiner* — Andrew Yang
*Assistant Examiner* — Diana S Jones
(74) *Attorney, Agent, or Firm* — William J. Sapone; Ware Fressola Maguire & Barber LLP

(57) ABSTRACT

A bone harvesting device is disclosed as including a drill body for drilling into bone, the drill body being rotatable about its central longitudinal axis, and a saw pivotable relative to the drill body about a pivoting axis parallel to the central longitudinal axis of the drill body, the drill body including a cavity which opens at a lower open longitudinal end of the drill body, and the saw being pivotable relative to the drill body between a first position in which the saw is clear of the lower open longitudinal end of the drill body and a second position in which the saw blocks part of the lower open longitudinal end of the drill body.

16 Claims, 33 Drawing Sheets

(56) References Cited

OTHER PUBLICATIONS

Taylor, Gregory, Intra-oral Autogenous Bone Grafting for Dental Implant Site Preparation, The Hong Kong Medical Diary, Mar. 2010, vol. 15, No. 3, pp. 12-14.

International Search Report, for PCT/CN2011/082328, 3 pages, mailed Mar. 8, 2012.

Supplemental European Search Report for corresponding EP application No. 11 84 2464, completed Jul. 17, 2014, 4 pages.

* cited by examiner

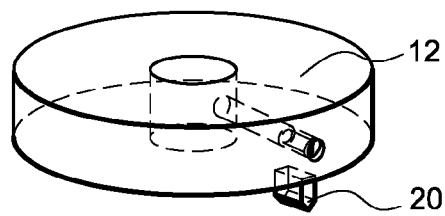
Fig.5A
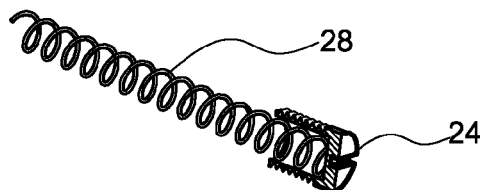
Fig.5B
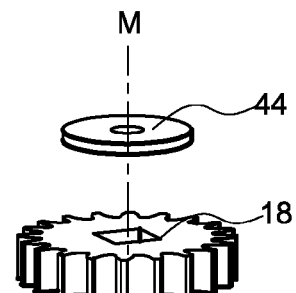
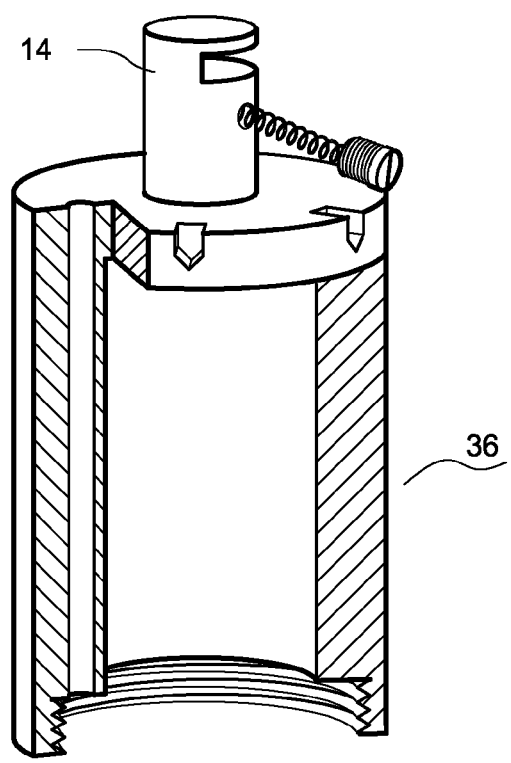
Fig.5C
Fig.5E
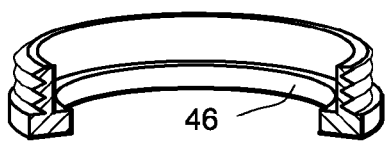
Fig.5D

BONE BLOCK

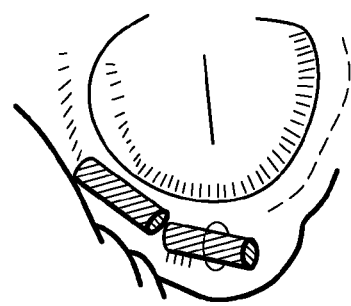 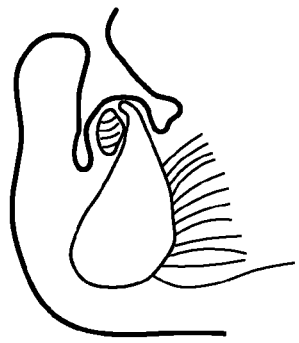
Fig.27A        Fig.27B
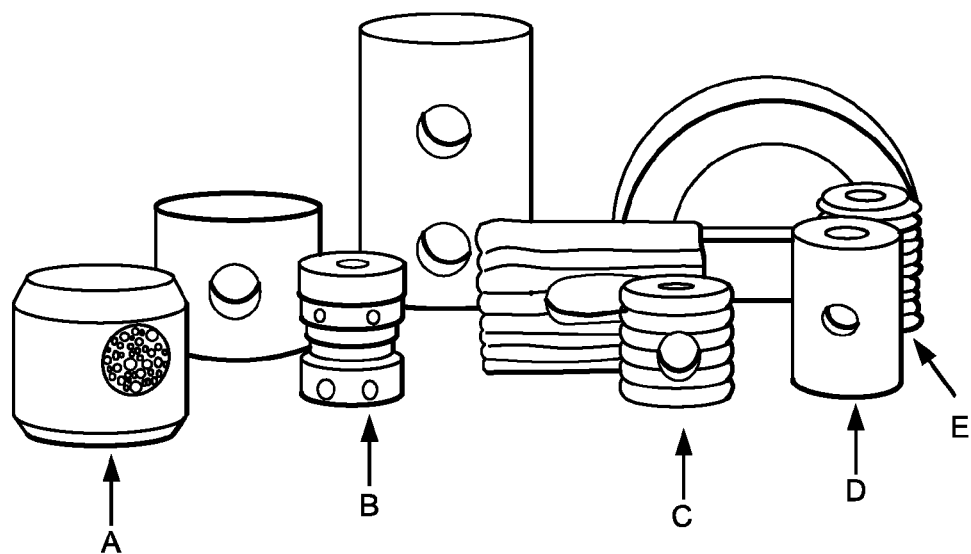
Fig.28

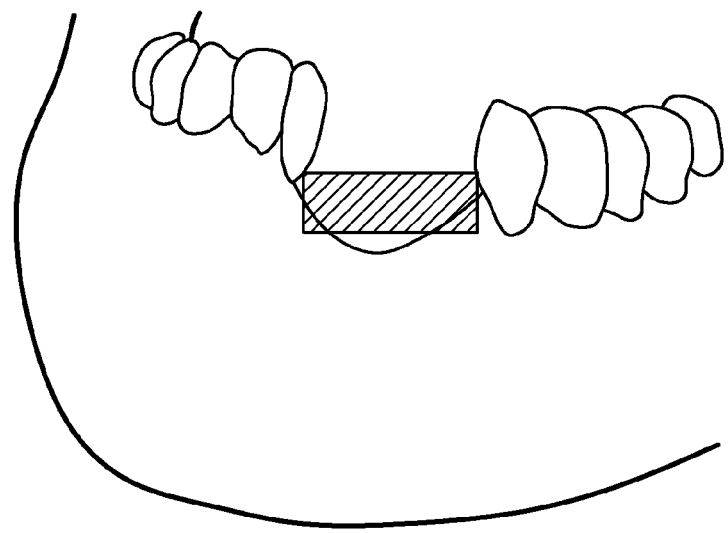
Fig.35
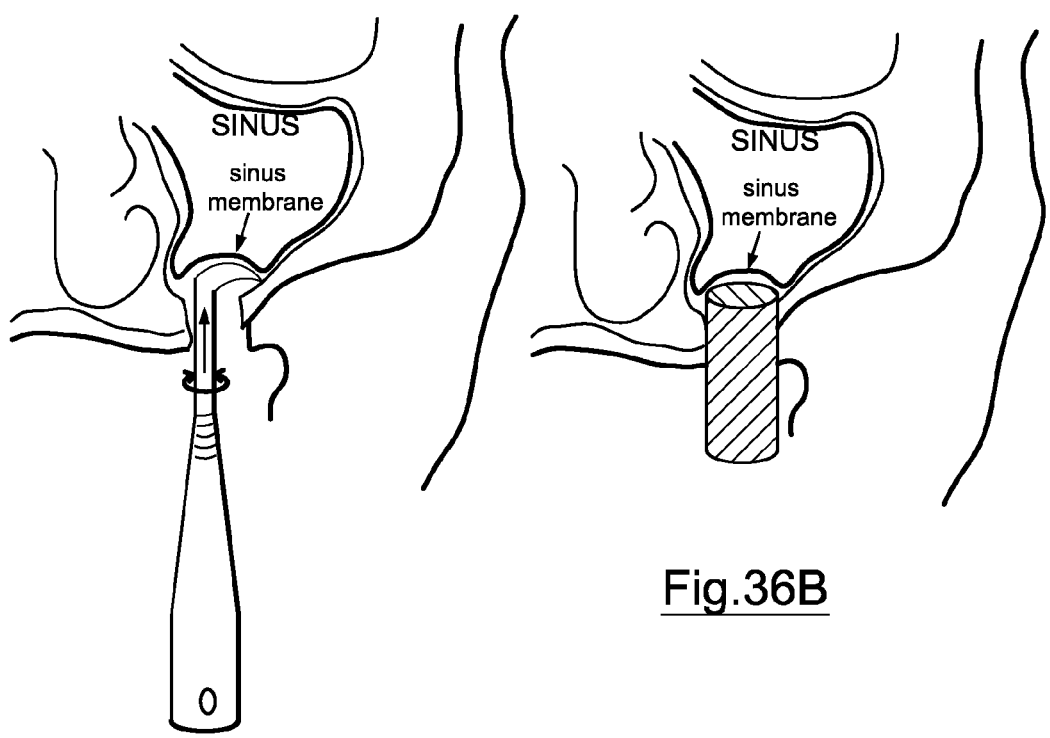
Fig.36B
Fig.36A

BONE BLOCK GRAFTS WIRED ON FOR CERVICAL FUSION. (NECK AREA)

SPLIT BONE BLOCK INTO TWO HALVES.

MATCHSTICK BONE GRAFTS

SPLIT BONE BLOCK INTO 2,4 OR 6 MATCHSTICKS

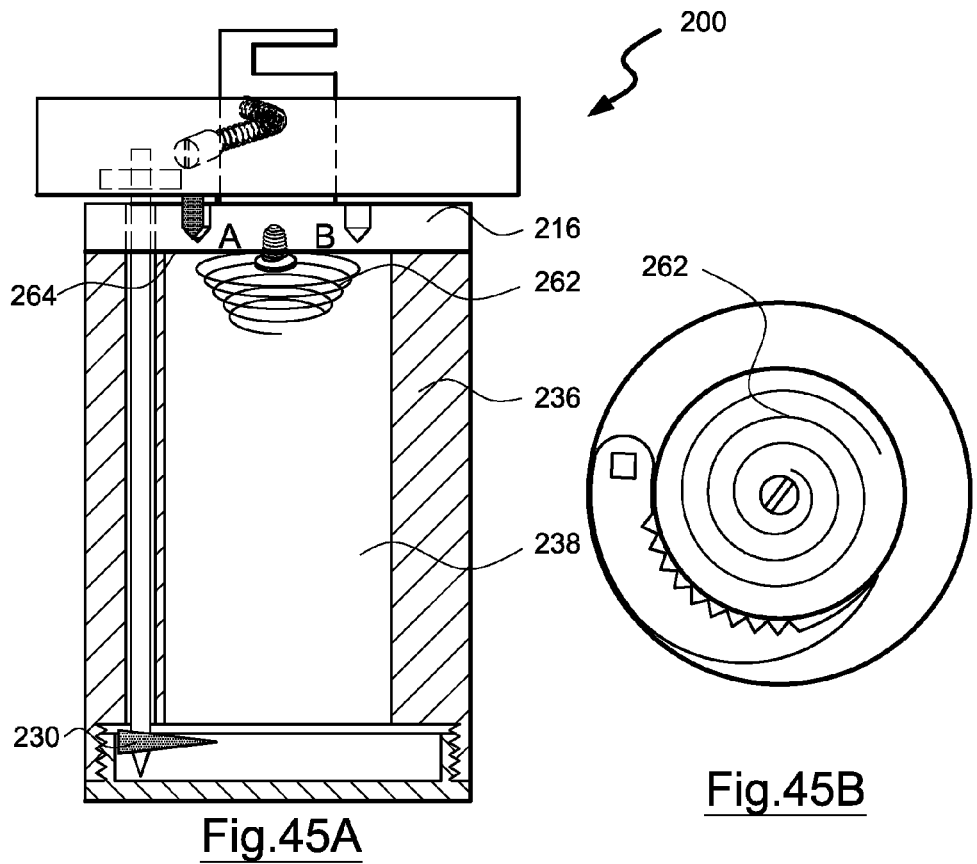
Fig.45A
Fig.45B
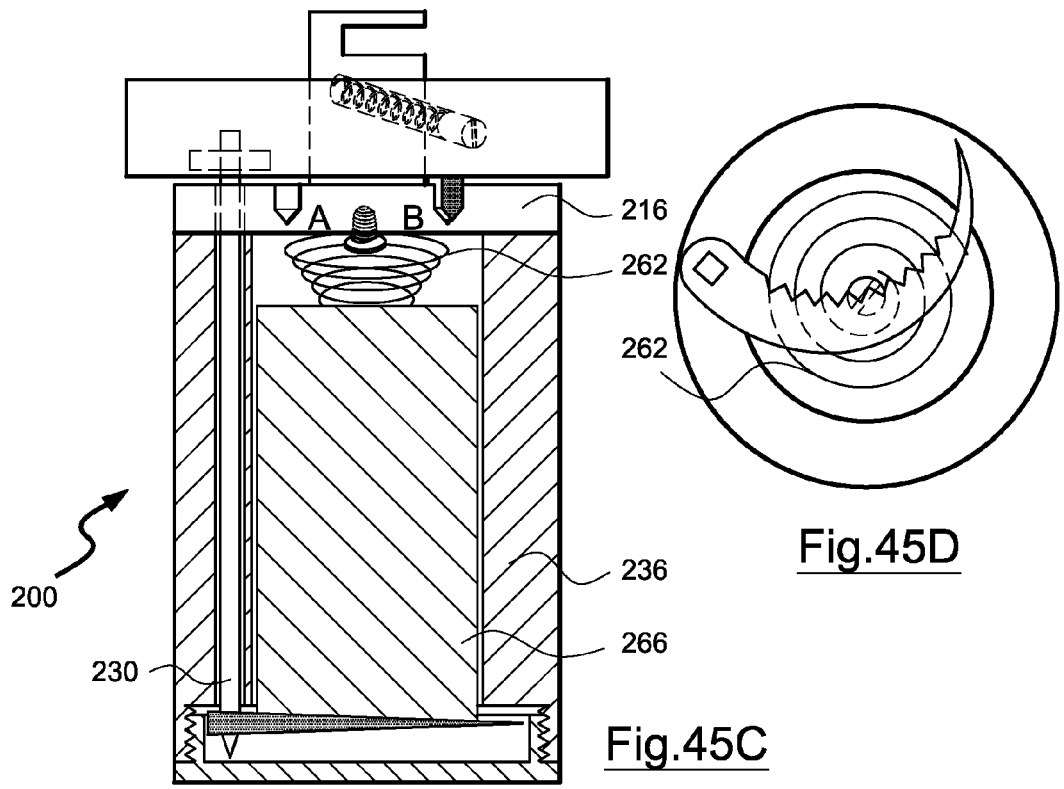
Fig.45C
Fig.45D

BONE HARVESTING DEVICE

TECHNICAL FIELD

This invention relates to a bone harvesting device, in particular such a device suitable for use in oral surgery and orthopaedic surgery.

BACKGROUND

Doctors that perform bone graft procedures are commonly orthopaedic surgeons, otolaryngology head and neck surgeons, neurosurgeons, craniofacial surgeons, oral and maxillofacial surgeons, periodontists and dentists. Surgeons use bone grafts to repair and rebuild diseased bones in the jaws, spine, hips, knees and other bones and joints.

Over 500,000 bone graft procedures are performed in the United States each year. The estimate cost of these operations approaches US$2.5 billion per year, and millions more world wide. At least 250,000 spinal fusions are performed in the United States each year, nearly all requiring implantation of bone graft material. The preferred technique for most of these operations is the transplantation of structured or morcellized autogenous corticocancellous bone from the iliac crest. Further, because of the increasing frequency of spinal fusion surgery during the 1990's, arthrodesis of the spine has become the most common reason for autogenous bone graft harvest. Spinal fusion is the joining or fusing of one or more vertebrae to reduce pain and stabilize the spine. During spinal fusion, a wide variety of implants, screws and cages may be used to enhance the fusion. However the fusion is only considered successful when the bones grow together biologically to form a solid mass. This fused connection is primarily achieved by the incorporation of a bone graft.

Another most common use of bone grafting is in the application of dental implants for the jaws, in order to restore the edentulous area of a missing tooth. Dental implants have increased exponentially in popularity over the past fifteen years, contributing to the significant increase in demand for bone grafting in the jaws, and this trend is projected to continue in the future. As for cleft palates, the obstructed airway which often results from repair of complete clefts is a source of upper respiratory tract infections, sinusitis and otitis media leading to poor physique, deafness, bronchitis, and other ailments besides handicapping the individual's exercise tolerance for life. It is extremely difficult to correct this by operations on the soft tissues alone despite the multiplicity of ingenious techniques. The expansion of the maxilla (palate) achieves this more completely and with more certainty and the operation is worth doing for this purpose alone. Rapid expansion of the collapsed maxilla is performed with orthodontic appliances, followed by bone grafting which provides and ensures its permanent stability, and reconstructing the defects. The main bone graft is best taken from the inner table of the ilium, and match stick bone pegs are included alongside to reinforce stability of the main graft.

The most critical problem during a dental implant placement is the reduced amount of available bone to support it and to achieve the necessary initial stability for osseointegration to occur. In many cases, the jawbones have been so severely destroyed by gum disease that the minimum available bone height and width required for accommodating the dental implant is often absent. Without bone grafting procedures to provide additional bone, many dental implant placements are not possible.

Bovine bone, i.e. cow bone, has become very popular, and commercially successful. It comes in particulate form and it is mixed with saline for the grafting of bony defects, or for grafting into the floor of the maxillary sinus to accommodate the dental implant. However, there are two problems associated with the use of animal bone. Firstly, bovine bone, like all commercial bone products, requires seven to twelve months to sufficiently consolidate to receive a dental implant. It has no living osteogenic cells, and the quality does not compare to the patient's natural vibrant and resilient bone, which when harvested, often contains healthy blood vessels, contributing to the ideal.

Secondly, there are concerns from the patients' point of view that it is of animal bone, and opens the risk of acquiring mad cow disease. There are other choice forms of bone, alloplasts like ceramic grafts, or hydroxyapatite and tricalcium phosphate, bioglass, etc. and so on, but they are mostly in particulate form and cannot provide the solid block of bone for tangible use. In addition, these are very expensive materials.

Allografts are bone tissues taken from human cadavers, and although these are treated by tissue freezing, freeze-drying, gamma radiation, electron beam radiation, ethylene oxide, etc., the risk of disease transmission is not completely removed; as in HIV, Hepatitis B and Hepatitis C, and other various pathogens. A case of death has been reported, in particular, a patient died of infection caused by Clostridium Sordellii within four days of the surgery, in November 2001, prompting investigations which revealed more cases of allograft-related infections.

Autogenous or autologous bone is the patient's own bone. In general, most patients prefer this prime choice. It is the ideal bone to use for bone augmentation in oral surgery, implant dentistry, orthopaedic surgery and wherever bone grafting is required in the human body. Autogenous bone is always regarded as the gold standard, and superior to all other alternative non-autogenous bone products. The greatest advantage is that autogenous bone provides osteogenic cells for phase I bone formation, and no immunologic response occurs. In fact autogenous bone is highly osteogenic and best fulfills the dental-grafting requirements of providing a scaffold for bone regeneration. In addition, it saves time. Whereas all commercial bone products require seven to twelve months to consolidate and fuse with the native recipient bone, autogenous bone does so in three months. Henceforth the provision of teeth onto dental implants into this bone can be accomplished in a much shorter time frame. In the operator's point of view, the time frame is an important factor, and would avoid the use of all such bone products as these would impose a significant prolonged time frame for the treatment case to be completed, and in many instances, up to a year. However, the complexity and risks of harvesting the patient's own bone currently render most dental operators unable to proceed at this point.

Typically autogenous bone grafts are taken from the pelvis or iliac crest. All bone requires blood supply to the transported site and bone grafts which already contain blood vessels is the ideal. Autogenous bone in solid block form is ideal for this reason, and it also contains bone morphogenetic proteins (BMP's), but in fact, autogenous bone possesses all of the characteristics required for new bone growth, namely, osteoconductivity, osteogenicity, and osteoinductivity.

The current procedure imposes the inevitable need for a second operation at a donor site, and with prior art tool, it is a traumatic and tedious process. Specialist oral surgeons are capable of harvesting autogenous bone from chosen donor sites in the patient's mouth. However the tedious and traumatic nature of the task also involves great risks of complications, being an invasive and often destructive process using prior art. Prior art tools include bone saws, bone drills, hammers and chisels, elevators to peel and lift out the bone block, and the trephine drill to define circular shapes of bone blocks which must subsequently be procured by free hand, with skill, using an array of various elevators.

Whereas the prior art standard trephine drill provides a roof and walls to confine the bone stud it creates, it does not provide a floor base to fully contain it, to support it and hence to harvest it.

As access is difficult for such a task, extensive incisions for large openings at the surgical site are often necessary, contributing to an increased size of the donor wound, and subsequent associated morbidity. With prior art bone harvesting tools, very often the tediously harvested block of bone has to be dramatically reduced and reshaped in order to fit the deficient bony site it is destined for, and bone is wasted in the process. Autogenous bone grafting has indeed excellent fusion rates and has become the gold standard by which all other biologics are measured. Many surgeons prefer autogenous bone grafts because there is no risk of the body rejecting the graft since it came from the patient's own body. The current disadvantage of autogenous bone grafting in orthopaedic surgery is the need for an additional operation which is currently traumatic. The pain and soreness can often last well after the surgery is healed, and there are possible complications such as increased blood loss and prolonged time in the operating room in about 10% to 35% of patients, and varying in severity in these cases, with the use of prior art.

As autogenous bone harvesting is associated with such untoward morbidities, and the use of alternatives of biological non-autogenous bone blocks have been reported to produce sporadic results of success, there exists a need to provide a bone harvesting device in which the aforesaid shortcomings are mitigated, or at least to provide a useful alternative to the trade and public.

SUMMARY OF THE INVENTION

According to the present invention, there is provided a bone harvesting device including means for drilling into bone, said drilling means being rotatable about its longitudinal axis, and cutting means pivotable relative to said drilling means about a pivoting axis substantially parallel to said longitudinal axis of said drilling means, wherein said drilling means includes a cavity which opens at at least one open longitudinal end of said drilling means, and wherein said cutting means is pivotable relative to said drilling means between a first position in which said cutting means is clear of said open longitudinal end of said drilling means and a second position in which said cutting means blocks at least part of said open longitudinal end of said drilling means.

BRIEF DESCRIPTION OF THE DRAWINGS

Bone harvesting devices according to embodiments of the present invention will now be described, by way of examples only, and with reference to the following drawings, in which:

FIGS. 5A to 5E illustrate in more detail various components of the device of FIG. 1;

FIGS. 27A and 28B illustrate a horizontal, in this case, the lateral (outer) ridge, grafting with a block of bone harvested by the device of FIG. 1;

FIG. 28 illustrates a sample of commercially available polymer-based bone graft substitutes in solid block forms, as produced by Orthovita Inc.;

FIGS. 29A and 28B illustrate the harvesting of a bone block from the iliac crest by the device of FIG. 1, which is immediately transported to the spine for a spinal fusion procedure, for permanently fusing together two or three spinal vertebrae of the spine, in which the initial stability is provided by a metal plate;

FIG. 35 illustrates the use of a block of bone harvested by the device of FIG. 1 in distraction osteogenesis;

FIG. 36A and 36B show insertion of a solid bone block harvested by the device of FIG. 1 into the sinus with or without perforation of the sinus membrane;

FIGS. 45A to 45D show a bone harvesting device according to a still further embodiment of the present invention.

DETAILED DESCRIPTION OF THE INVENTION

Figure 1:
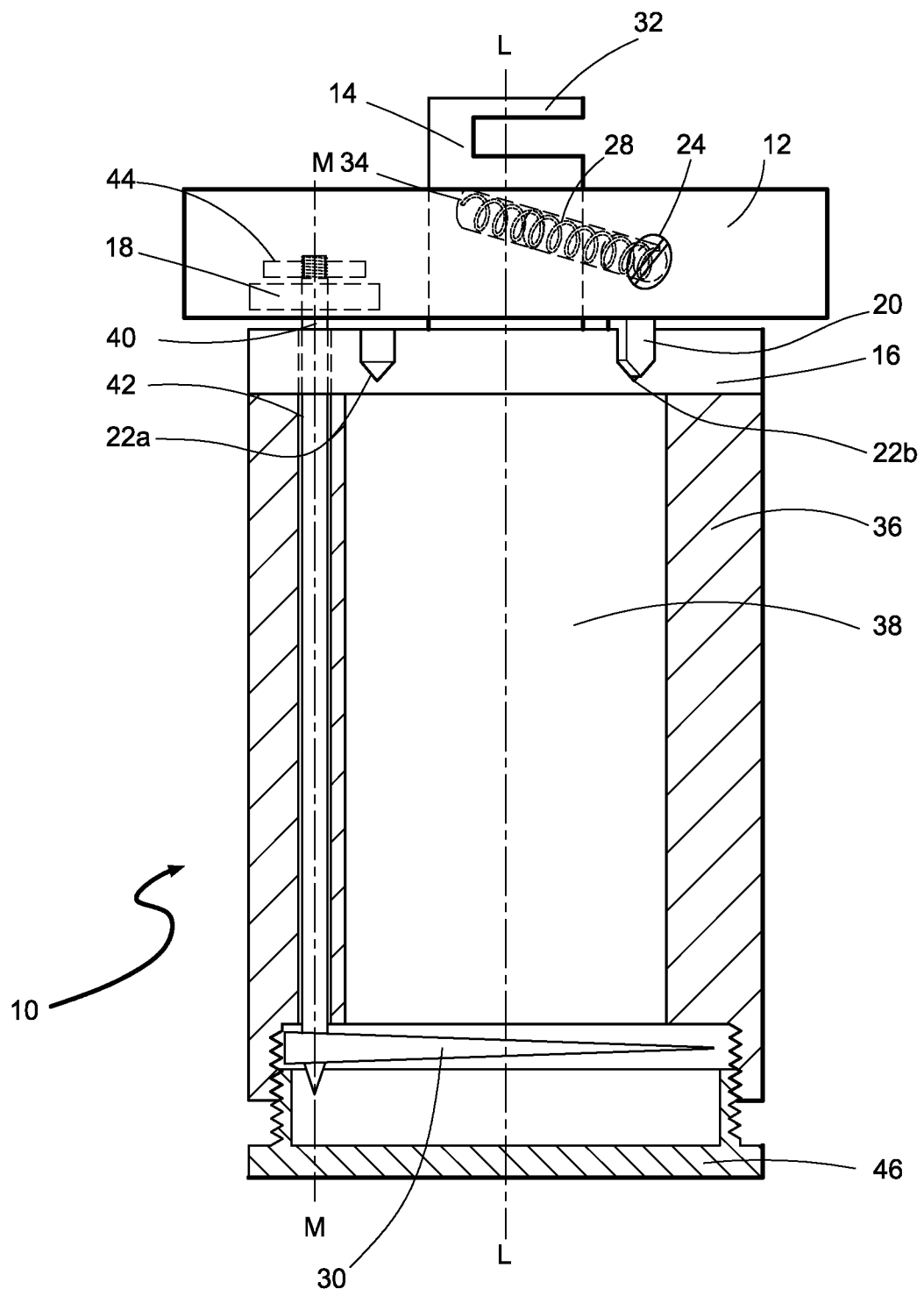
FIG. 1 is a schematic front view of a bone harvesting device according to an embodiment of the present invention.
Figure 2:
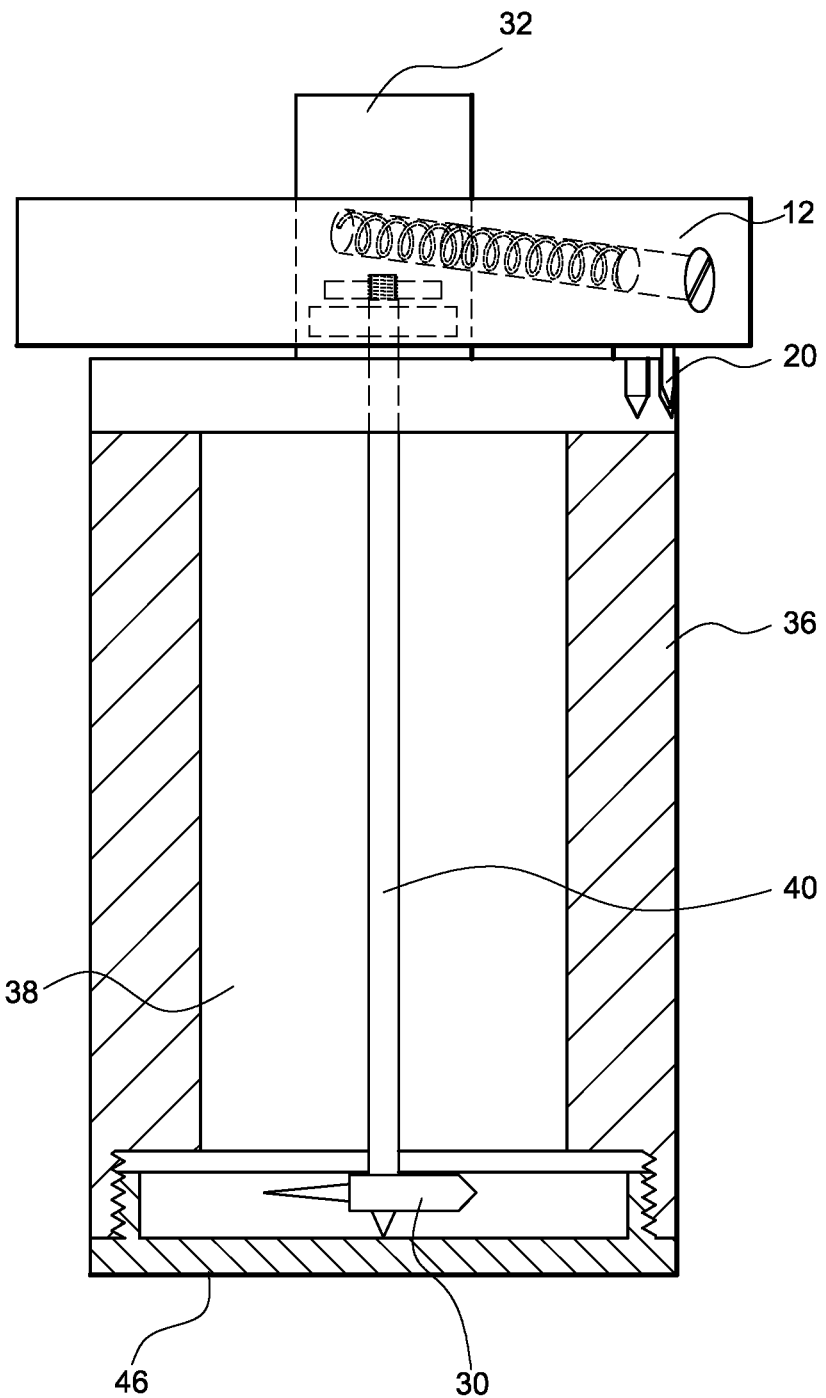
FIG. 2 is a schematic side view of the device of FIG. 1.

A bone harvesting device according to an embodiment of the present invention is shown in FIGS. 1 and 2, and generally designated as 10. The various components forming the device 10 are all separable from one another and thus individually replaceable. The device may be used with any standard hand piece.

The device 10 has an actuation ring 12 which is a large and thick diameter ring with a circular hole at its centre. The actuation ring 12 is placed loosely around a drill shaft 14. The ring 12 can move freely relative to the drill shaft 14, including rotating about the drill shaft 14 about a common central longitudinal axis L-L, and moving up and down along the drill shaft 14. The ring 12 usually rests on a drill shoulder 16 which is of a smaller diameter than the ring 12. The outer rim surface of the ring 12 is smooth, but its inner rim surface is serrated with vertical teeth. The ring 12 is in mesh with a wheel 18 such that the vertical teeth of the inner rim surface of the ring 12 are in constant engagement with vertical mechanical teeth of the outer rim surface of the wheel 18. Such an arrangement controls the rotational movement and position of the saw 30, to be discussed below.

There is a triangular protrusion 20 at the base of the ring 12 which is engageable with either of two triangular slots 22a, 22b on the drill shoulder 16. These two slots 22a, 22b are suitably separated apart on the drill shoulder 16. The protrusion 20 is like the bottom half of a hexagon and includes vertical flat edges above the triangle to effect engagement with the slots 22a, 22b.

Directly above the triangular protrusion 20 is a cradle screw 24 which receives one longitudinal end of a spring 28. The actuation ring 12 is simply retained to the rest of the device 10 by the firm seating of the spring 28 within the cradle screw 24. The cradle screw 24 is above the triangular protrusion 20.

More particularly, the cradle screw 24 is an end tunnel structure in the form of a hollow screw within the ring 12 and receives one longitudinal end of the spring 28. The cradle screw 24 can be unscrewed and removed from the side surface of the ring 12, together with the spring 28 within it. The head of the hollow screw 24 may be fastened onto or unfastened from a side surface of the ring 12 when the protrusion 20 is engaged with the slot 22b. When the ring 12 is in this position, the spring 28 is straight, and when the cradle screw 24 is unfastened and removed together with the spring 28, the retainment of the ring 12 is also released, thus allowing the ring 12 to be removed out from the drill shaft 32, enabling access for the replacement of a saw 30 and a rod 40 with which the saw 30 is engaged. Basically, the saw 30 is a bone micro-saw.

A drill shaft 32 is provided at an upper end of the device 10. The drill shaft 32 contains within it a shaft tunnel 34 which is slanted relative to the longitudinal axis L-L by about 75°. This shaft tunnel 34 has an inner closed end and an outer open end. One longitudinal end of the spring 28 is firmly attached to the inner closed end of the tunnel 34, and, as mentioned above, the other longitudinal end of the spring 28 is fixed within the cradle screw 24. The arrangement is such that, when the triangular protrusion 20 is engaged in the triangular slot 22b, the spring 28 is straight.

If the actuation ring 12 is moved along the drill shaft 14 and axially away from the drill shoulder 16 and the drill body 36, the spring 28 tends to draw the ring 12 back towards the drill shoulder 16 and the drill body 36. The spring 28 thus biases the actuation ring 12 towards the drill shoulder 16 and the drill body 36, and reinforces the engagement of the triangular protrusion 20 within the respective slots 22a, 22b.

The device 10 includes a drill body 36. Venting holes (not shown) may be provided through the drill body 36 to allow saline water coolants to enter a drill cavity 38 in the drill body 36 during operation, which keeps the bone stud cool and flushes away debris. After operation, the harvested bone is contained within the drill cavity 38.

The wheel 18 is fixed to the top end of the rod 40, and directly above the opening of a drill tunnel 42 which runs through both the drill body 36 and the drill shoulder 16. As discussed above, the outer surface of the wheel 18 has vertical serration of mechanical teeth in constant contact and engagement with vertical serration of mechanical teeth of the inner surface of the rim of the ring 12. A screw ring 44 secures the top of the rod 40, with a circular thread finish, to the wheel 18, via its central screw hole.

Rotation of the ring 12 relative to the drill body 36 about the longitudinal axis L-L will bring about rotation of the wheel 18. On the other hand, the ring 12 may be moved along the drill shaft 14 towards and away from the drill shoulder 16, without bringing about any movement on the part of the wheel 18. In particular, the respective vertical mechanical teeth of the ring 12 and the wheel 18 are free to slide lengthwise along and relative to each other while not causing any relative rotational movement between the ring 12 and the wheel 18.

The rod 40 is a long rectangular rod which passes down within the drill body 36 and through the drill tunnel 42. An end of the saw 30 is fixedly connected close to a bottom end of the rod 40. A top end of the rod 40 is fixedly connected to the wheel 18. The rod 40 passes down within the drill tunnel 42 through the drill body 36, and passes out of the drill tunnel 42 near the end of the drill body 36 to be connected at its lower end with the saw 30. Rotation of the wheel 18 will thus effect rotation of the saw 30. The rod 40 functions also as a hinge for the swiveling/rotational movement of the saw 30, since the rod 40 is connected perpendicularly to one end of the saw 30. Thus, when the rod 40 is positioned vertically, the saw 30 lies flat. The rod 40 passes through and beyond the saw 30 and finishes as a sharp point, which rests on a platform provided by a drill end 46 which is threadedly engaged with a lower open end of the drill body 36. The rod 40 essentially acts as a spindle.

The top of the rod 40 passes through a hole of the wheel 18, and finishes above as a circular screw-threading, which is received by a screw hole of the screw ring 44. The screw ring 44 fastens and secures the rod 40 to the drill body 36. In essence, removing the ring 12 and unfastening the screw ring 44 and the drill end 46 will allow replacement of the rod 40 and the saw 30.

The saw 30 has a base end and a tip end, and is pivotable relative to the drill body 36 about a longitudinal axis M-M of the rod 40 (which is parallel to the central longitudinal axis L-L of the drill body 36) to open and partly close a lower open end of the drill cavity 38 of the drill body 36. The rod 40 is connected to a flat surface of the base end of the saw 30 at 90°. The flat surface of the saw 30 is parallel to the horizontal, and cutting teeth of the saw 30 face towards the open end of the drill body 36. The rod 40 and the saw 30 are fabricated in one cast component which can be removed and replaced.

The slimmer and finer the whole cast micro spindle and saw component (namely, the rod 40 and the saw 30) can be fabricated, the thinner can be the wall of the drill body 36, so as to maximize the diameter of the drill cavity 38 within the drill body 36, and thus to accommodate a bone block of a larger diameter. This reduces bone wastage and provides efficiency to attain larger bone blocks within the device 10. This whole cast component is at the heart of the present invention, whose operation and movement being controlled by the actuation ring 12.

Although one may question the feasibility of confining a micro spindle and saw component in the drill body 36, as in the one-cast vertical rod and transverse saw, one must first consider the factual anatomical dimensions of the jaws. As the standard conventional bare trephine drill must be small to carve out small blocks of bone which can be physically procured by the hand of the operator, it cannot be conceived to conceal any additional components within it. However, in the molar area of the jaws, larger trephine drills may be employed to house the components required because the molar teeth embedded in the jaws measure 11 mm in diameter and their roots extend 14 mm into the jawbone, not to mention being surrounded by more bone around them. When their sockets are filled with new bone subsequent to their extractions, the cylindrical block of bone to be harvested from these areas approximates to such dimensions and allows device 10 of comparable sizes to be used. In such areas, it is feasible for micro spindle and saw components of up to 2 mm to be incorporated, if necessary. As a standard dental implant is of a diameter of 4.1 mm and implants of a smaller diameter (e.g. of 3.3 mm) are also available, a block of bone of a diameter of 6 mm to 8 mm (as harvested by the device of FIG. 1) will suffice for the purposes. However, in the case of the posterior iliac crest of the hips, there is ample room for all components for use of a suitably sized version of the device 10 of the present invention.

The drill end 46 is a separable end piece of the device 10 which screws onto the lower end of drill body 36. This drill end 46 serves two purposes. When it is unfastened and separated from the drill body 36, such allows access for removal of the rod 40 and the saw 30. When the device 10 is in use, the drill end 36 provides an internal platform to support the sharp pointed end of the rod 40 for pivotal movement of the rod 40 (and thus the saw 30) relative to the drill body 36.

The incorporation of the saw 30 is an important feature of this invention because it serves not only to sever the end of the bone stud, at a chosen cut-off point, but also to afterwards serve as a floor base of the drill cavity 38, fully containing the bone block within, and supporting it as it is lifted out from its original site, completely concealed in the drill cavity 38 of the drill body 36 of the device 10.

Figure 3A:
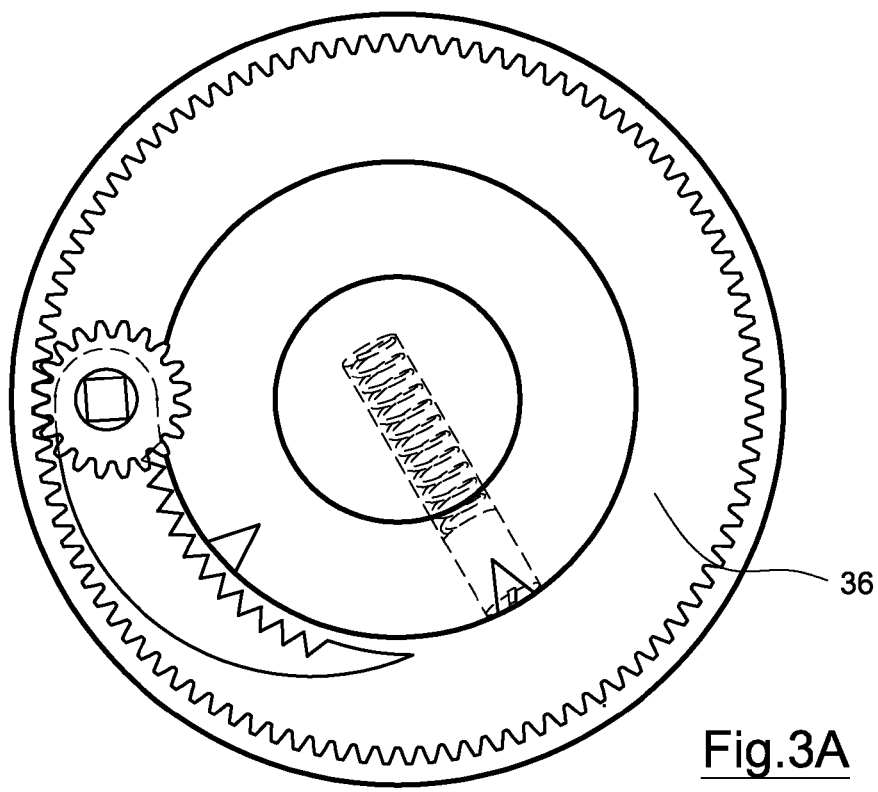
FIG. 3A is a schematic top view of the device of FIG. 1 with the saw in a closed position.
Figure 3B:
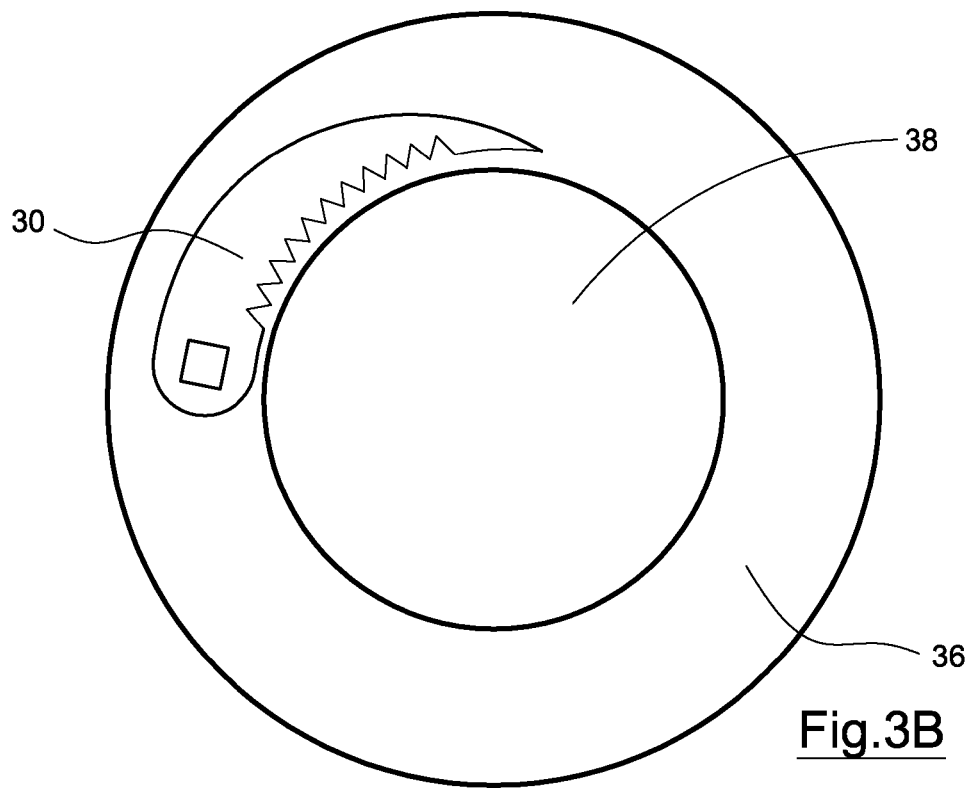
FIG. 3B is a schematic bottom view of the device of FIG. 3A.
Figure 4A:
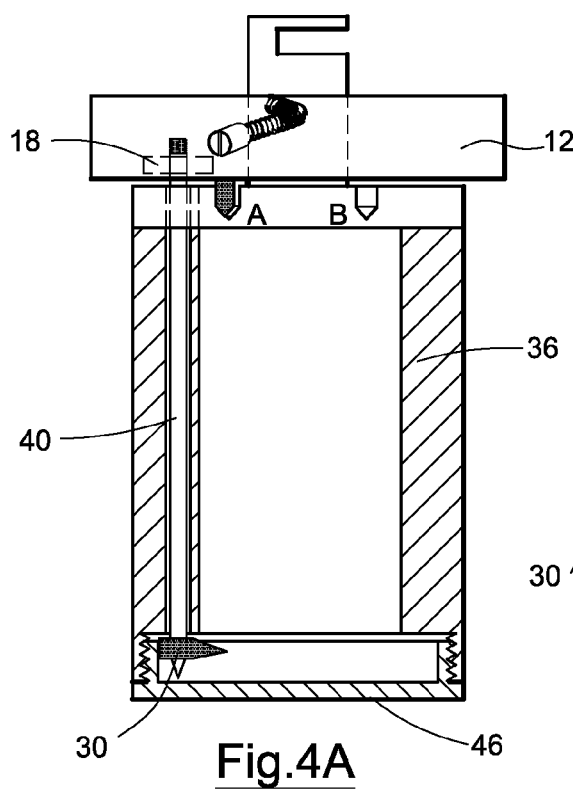
FIGS. 4A to 4D illustrate the relationship between the position of the actuation ring and the position of the saw of the device of FIG. 1.
Figure 4B:
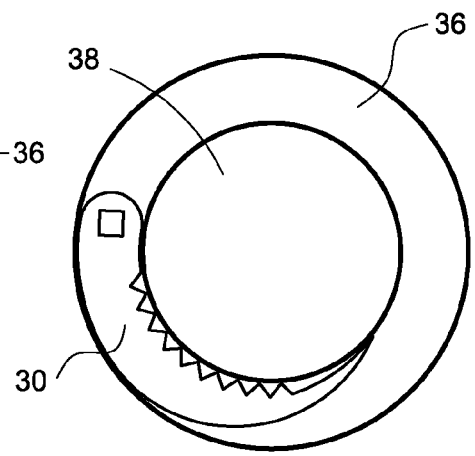
Figure 4C:
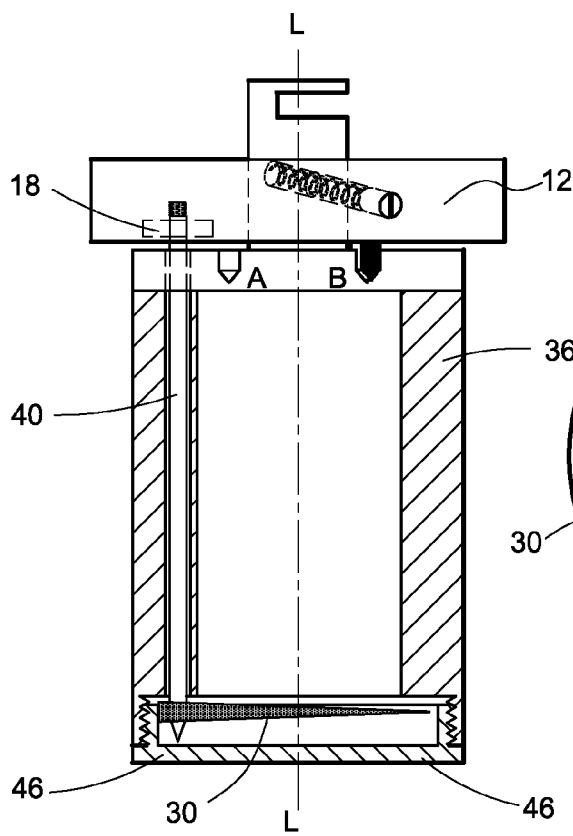
Figure 4D:
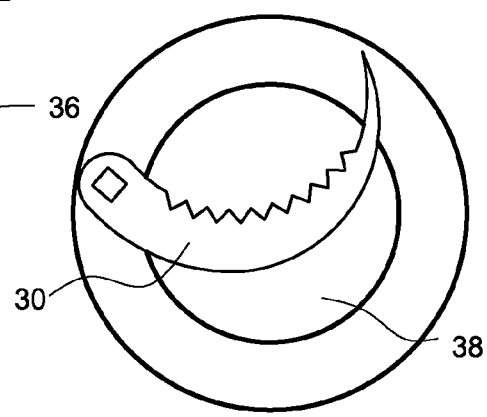

When the actuation ring 12 is positioned relative to the drill shoulder 16 such that the protrusion 20 is received within the slot 22a (as shown in FIG. 4A, and called the "A Position"), the saw 30 is totally clear of the open end of the drill cavity 38 of the drill body 36, as shown in FIGS. 3A, 3B and 4B. When the actuation ring 12 is rotated about its central longitudinal axis L-L relative to the drill body 36 and the drill shoulder 16 such that the protrusion 20 travels on and along the drill shoulder 16, until the protrusion 20 is received within the slot 22b of the drill shoulder 16 (as shown in FIG. 4C, and called the "B Position"), the wheel 18, with the rod 40 with which it is fixedly engaged, is caused to rotate about the longitudinal axis M-M of the rod 40, to bring about corresponding rotational/swivelling movement of the saw 30 to the position as shown in FIG. 4D, in which the saw 30 blocks part of the open longitudinal end of the drill cavity 38 of the drill body 36 of the device 10. It is preferable to arrange the components such that when the saw 30 blocks part of the open longitudinal end of the drill cavity 38 of the drill body 36, it blocks the centre point of the open longitudinal end of the drill cavity 38, as in the case of FIG. 4D.

FIGS. 5A to 5E respectively show in more detail the structure and arrangement of the actuation ring 12, spring 28, cradle screw 24, drill body 36, drill shaft 14, drill end 46, rod 40, saw 30, wheel 18 and screw ring 44 of the device 10.

When the device 10 is in the configuration as shown in FIGS. 4A and 4B, the protrusion 20 of the actuation ring 12 is received within the slot 22a on the drill shoulder 16 which is fixedly engaged with the drill body 36. The spring 28 biases the ring 12 towards the drill shoulder 16, thus maintaining the engagement between the protrusion 20 and the slot 22a, and preventing the ring 12 from exhibiting any rotational movement relative to the drill body 36.

Figure 6:
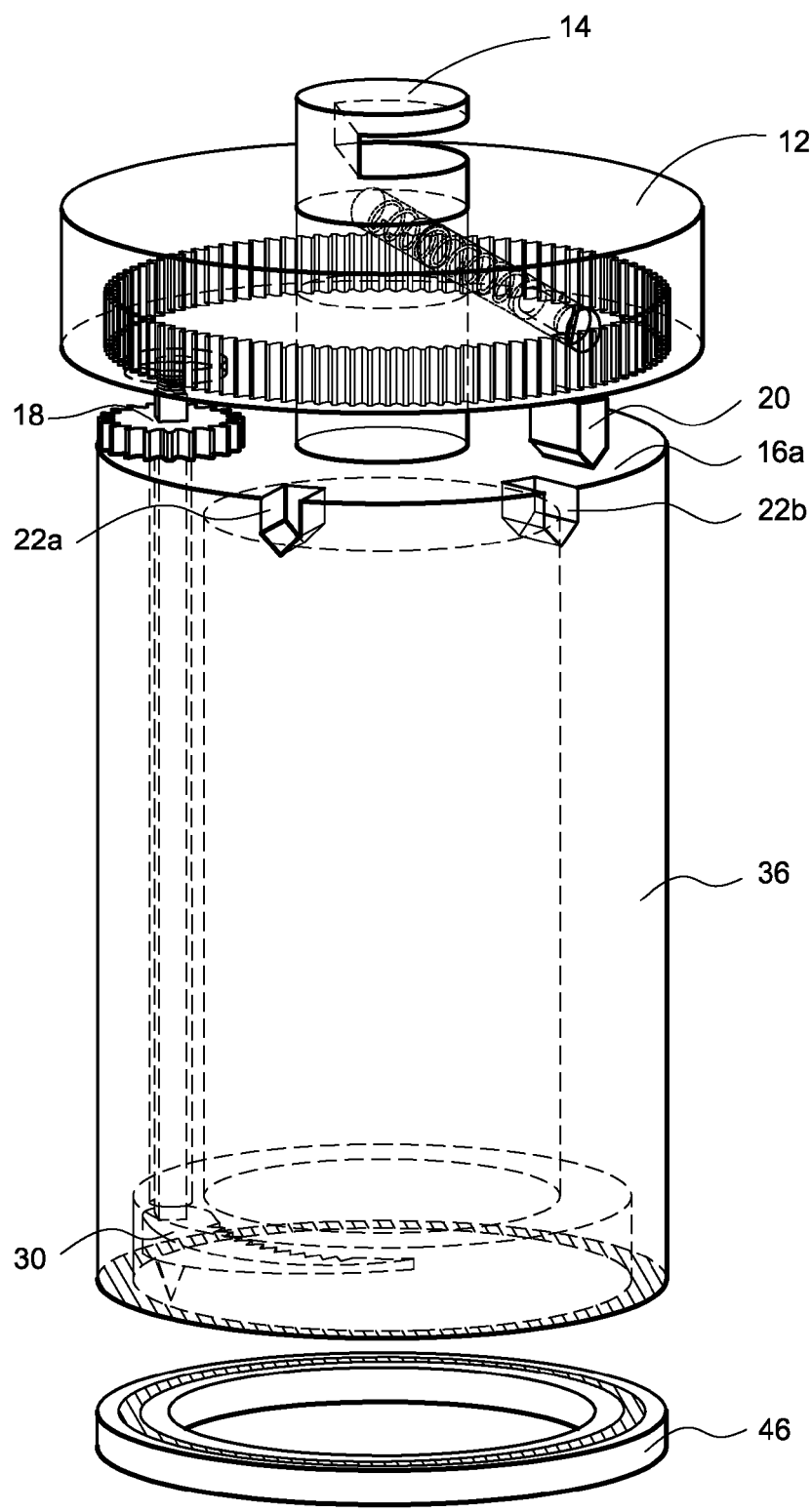
FIG. 6 illustrates in more detail the arrangement of the components of the device of FIG. 1.

The ring 12 may be moved (e.g. by a user or when the drill body 36 reaches a predetermined depth into the bone) axially away from the drill shoulder 16 against the biasing force of the spring 28, thus releasing the lock between the protrusion 20 and the slot 22a. Once the protrusion 20 is clear of the slot 22a, it rests on and slides along an upper surface 16a of the drill shoulder 16. Under the biasing force of the spring 28, the ring 12 rotates relative to the drill shoulder 16 (and the drill body 36) about the central longitudinal axis L-L, such that the protrusion 20 moves towards the slot 22b on the upper surface 16a of the drill shoulder 16, as shown in FIG. 6. During this rotational movement of the ring 12, the wheel 18 which is in mesh with the ring 12 is also brought into rotational movement about the axis M-M of the rod 40 with which it is fixedly engaged. The rotational movement of the rod 40 causes the saw 30 to swivel from its position as shown in FIG. 4B to the position as shown in FIGS. 4D and 6.

It should be noted that when the protrusion 20 is received within the slot 22b, the spring 28 also biases the ring 12 towards the drill shoulder 16 and thus maintains the engagement between the protrusion 20 and the slot 22b. The ring 12 is thus also prevented from exhibiting any rotational movement relative to the drill body 36. This means that the saw 30 will remain in the position in which it blocks part of the open longitudinal end of the drill body 36 unless a user moves the protrusion 20 back to engage with the slot 22a. Both the slots 22a, 22b are stable positions in which the protrusion 20 may remain.

If a user wishes to move the protrusion 20 back to engage with the slot 22a, he/she may move the ring 12 axially away from the drill shoulder 16 against the biasing force of the spring 28, thus releasing the lock between the protrusion 20 and the slot 22b. Once the protrusion 20 is clear of the slot 22a, a user may rotate the ring 12 (against the biasing force of the spring 28) relative to the drill shoulder 16 (and the drill body 36) about the central longitudinal axis L-L to move the protrusion 20 towards the slot 22a on the upper surface 16a of the drill shoulder 16. Once the protrusion 20 is engaged with the slot 22a, the ring 12 is allowed to move towards the drill body 36 under the biasing force of the spring 28. During this rotational movement of the ring 12, the wheel 18 which is in mesh with the ring 12 is also brought into rotational movement about the axis M-M of the rod 40 with which it is fixedly engaged. The rotational movement of the rod 40 causes the saw 30 to swivel from its position as shown in FIGS. 4D and 6 to the position as shown in FIG. 4B.

It can be seen that when the protrusion 20 of the actuation ring 12 is received within either the slot 22a or the slot 22b, the ring 12 is locked against rotational movement relative to the drill body 36 between the A Position and B Position. This also means that the saw 30 is locked against any movement relative to the drill body 36 when the protrusion 20 is received within either of the slots 22a, 22b.

Figure 7A:
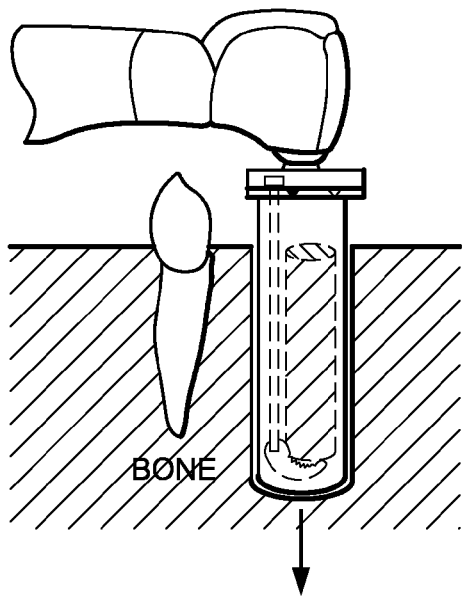
FIGS. 7A to 7D illustrate the process of harvesting a block of bone by the device of FIG. 1.

FIGS. 7A to 7D show steps of using the device 10 according to this invention, in which the device 10 is engaged with a hand piece 48. As shown in FIG. 7A, the actuation ring 12 is lifted up from its seated position in which the protrusion 20 is engaged with the slot 22a, then rotated clockwise (when viewed from above) until the protrusion 20 is engaged in the slot 22a. This process can be referred to as the winding-up of the ring 12. The drilling then begins downwards into the jawbone of a patient. This downward drilling creates a circular block of bone, whose length is determined by the depth of this drilling.

Figure 7B:
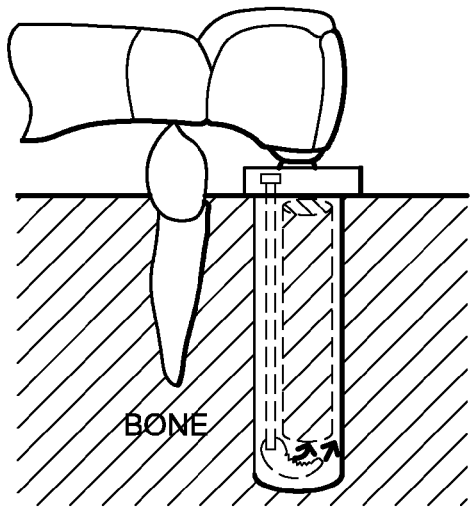

As shown in FIG. 7B, when the bottom of the outer edge of the actuation ring 12 impacts the top of the bone ridge, the ring 12 is abruptly disengaged from the drill shoulder 16, such that the ring 12 begins unwinding, rotating anti-clockwise (when viewed from above) under the biasing force of the spring 18, whereby the protrusion 20 moves towards the slot 22b. At the same time, the saw 30 is swiveled towards the open end of the drill cavity 38, and the drill body 36 is held at this preset depth level. This rotation serves mainly to drag the saw 30 around the base of the block of bone to close in transversely towards the central longitudinal axis L-L, to sever the block of bone.

Figure 7C:
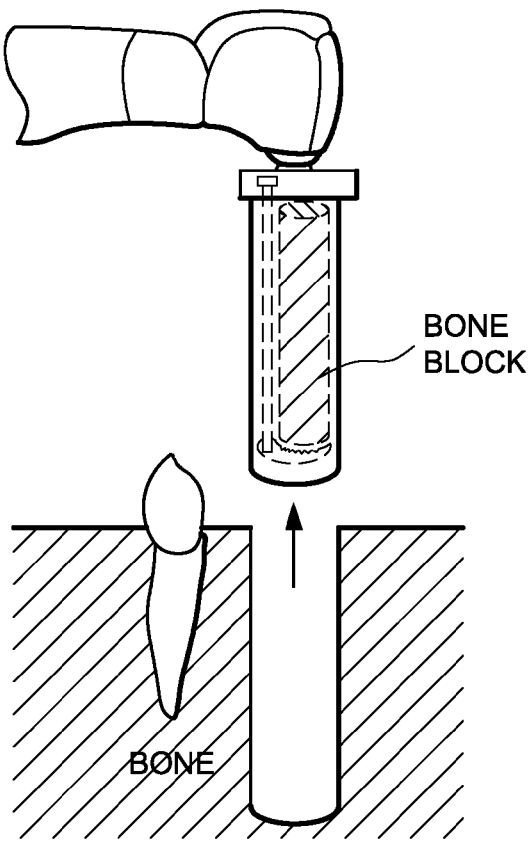

As shown in FIG. 7C, when the ring 12 is rotated to the position in which the protrusion 20 is immediately above the slot 22b, the ring 12 automatically snaps-in and the protrusion 20 firmly engages into the slot 22b, and the drilling can be stopped. The operator can also feel the sudden lowered resistance of the drill rotation as the drill body 36 rotates freely once the bone block is fully severed. With the bone block now contained inside the drill cavity 38, and the saw 30 is situated across the bottom of the bone block thus created, now providing its support, it is lifted out, creating a clean-cut socket in the bone.

Figure 7D:
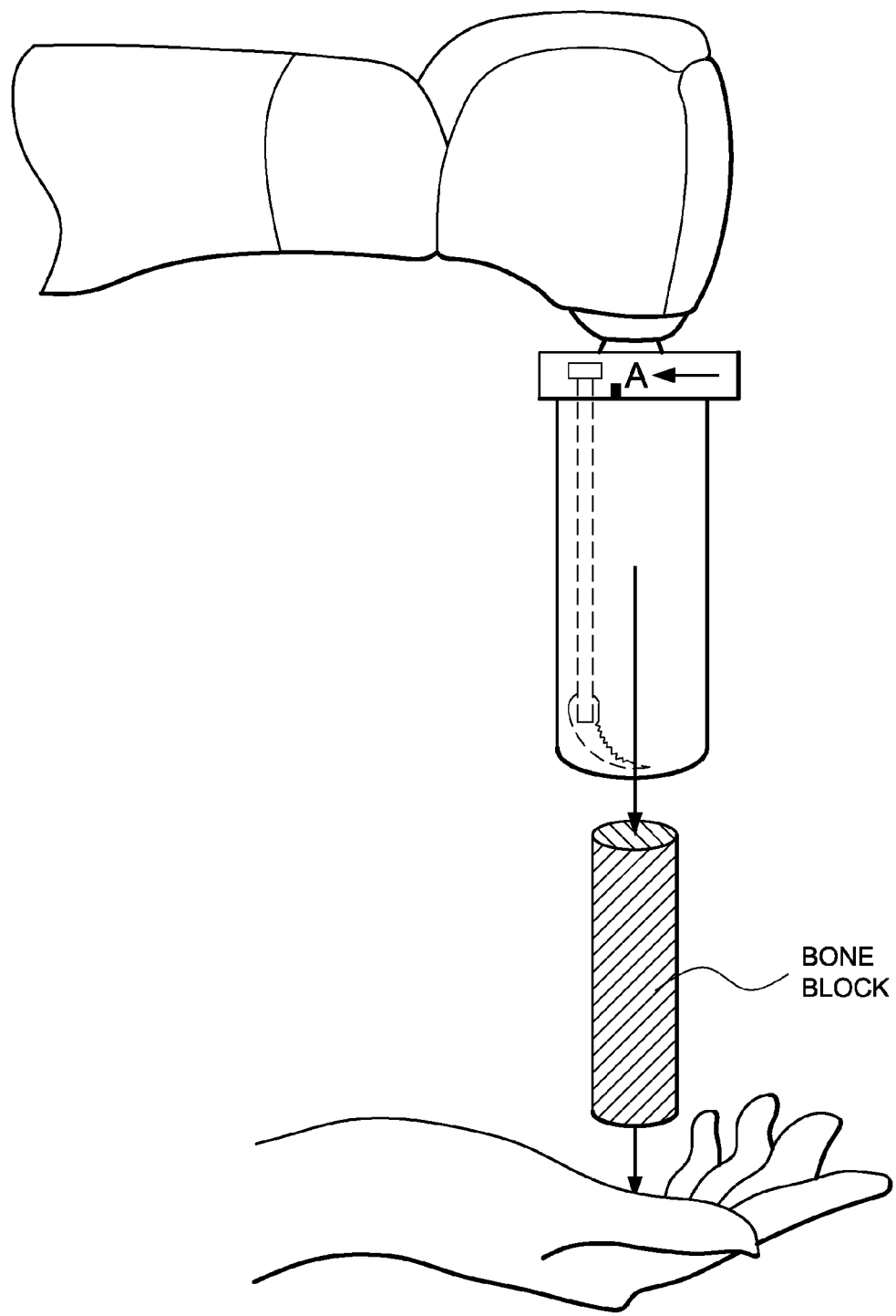

Turning now to FIG. 7D, the ring 12 is rotated back (clockwise), thus rotating the saw 30 back to the original position as in FIG. 4B, and allowing the bone block contained in the drill cavity 38 to fall out. The device 10 is now ready for the next round of operation.

To further describe the use of the device 10 in practice, let us assume that an operator would like to harvest a bone block of a length of 10 mm. Firstly, the operator winds up the ring 12 and firmly locks it in the A Position, then makes a tiny incision at the top of the gums, under a local anesthetic. The operator then uses the device 10 fitted onto a hand piece to drill down into the bone at 2-3 mm increments, push-stall, push-stall, push-stall, each time as one stalls, the drill friction is diminishing as bone around the drill body 36 is eliminated, and the drill body 36 rotates in free space. The intermittent stalling allows time for water to cool the friction heat amidst the drilling, and to flush away the debris. The drill body 36 may have markings on its outer surface to indicate the depth of drilling. The drill body 36 rotates frictionlessly at this point until the ring 12 suddenly springs-up. Then, new friction is suddenly felt at the drill tip, as the saw 30 at the tip of the drill body 36 squeezes on the bone stud created by the drill body 36. Then, the operator steps-on-it without pushing down on the device 10. When this final friction is also cleared, the operator can lift the device 10 out of the mouth, and a block of autogenous bone of a length of 10 mm is fully contained within the drill cavity 38 of the device 10, ready to be delivered by the device 10.

Figure 8:
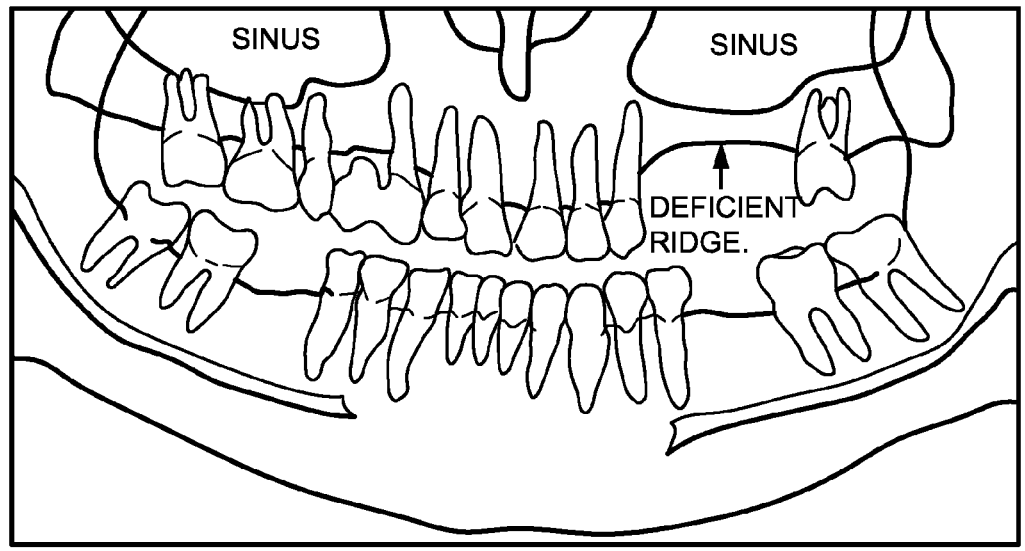
FIGS. 8 to 9B illustrate an example case in which the device of FIG. 1 is used.
Figure 9A:
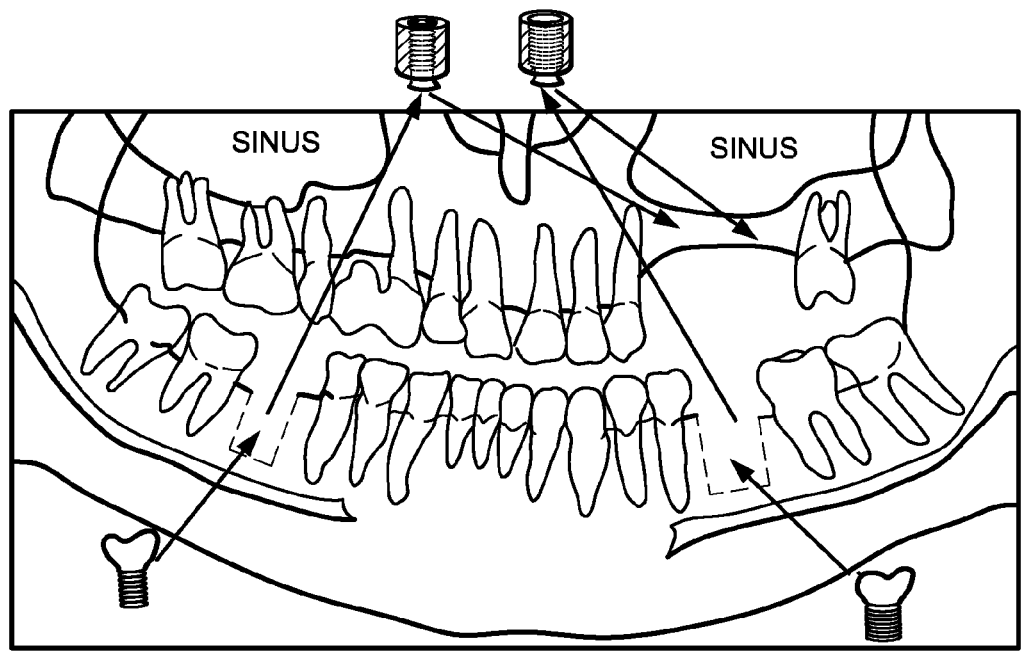
Figure 9B:
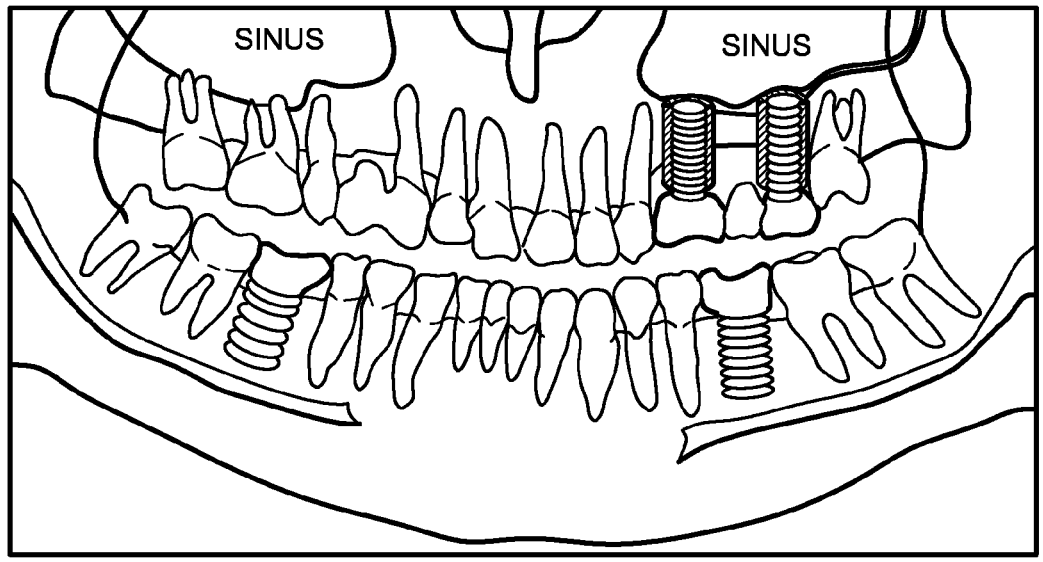

In the example as shown in FIGS. 8 to 9B, our attention is focused on the deficient ridge in the upper left molar region, just below the maxillary sinus. For this case, we will choose donor bone blocks from the underlying bone areas of both of the missing lower first molar tooth, as shown on FIG. 9A. We can effectively carve out two suitably sized autogenous blocks of bone from these missing lower first molar sites. In particular, with the use of the device 10 we can harvest two blocks of autogenous bone from these areas in the procedure previously described. The device 10 conserves bone with more certainty as it is physically impossible to drill extensively beyond the boundary limits of this device 10. The ring 12 and the roof of the drill cavity 38 both serve to limit the depth of the drilling, to avoid damage to vital structures, such as the inferior alveolar nerve in the lower jaw, or at the iliac crest, to prevent perforation at the medial aspect which damages the iliacus muscle, and to limit involvement of the peritoneum.

We then move on to the sinus grafting procedure at the upper deficient ridge site, and to prepare two smaller diameter circular holes at the floor of the left maxillary sinus, for receiving insertion of the two bone blocks just obtained from the lower jaw. The aim here is to produce a tightly matching fit. At the upper left deficient ridge, we can slowly and carefully insert the two cylindrical bone blocks, rotating each slowly inwards by hand via the beaks of a pair of dental forceps, into the holes prepared.

There should be a friction-fit feel to this process, and by slowly tapping the blocks in as is normally practiced for inserting any dental implant, as with delicate skill and care. The aim is to have each bone block suspended in the native bone, exactly half-way, with a slight protrusion at one end into the sinus, either pushing up the Schneiderian membrane and supporting it, or even perforating through it. Slight penetration into the sinus, whether by bone blocks or implants, in fact bears no consequences. The other end of the bone block protrudes slightly into the mouth.

Essentially the bone block is punched-in through drilled holes at the floor of the sinus and suspended half-way up via its congruous fit, with or without implants embedded in them, and either perforating or supporting the sinus membrane lining, which is carpeting the floor of the sinus.

Effectively there is the congruous frictional contact of the bone block at its mid-portion with the native bone of the deficient ridge, as shown in FIG. 9B, which is the key to this grafting success. This friction-fit omits the need for bone screws and bone pins for achieving retention and stability, as conventionally required for block bone grafting. This so-called 'stud-in-hole' technique is facilitated with the use of the device 10, which produces the unique shape of bone blocks in the form of "studs". This device 10 can provide studs of bone in full completeness, and as predetermined.

Figure 10A:
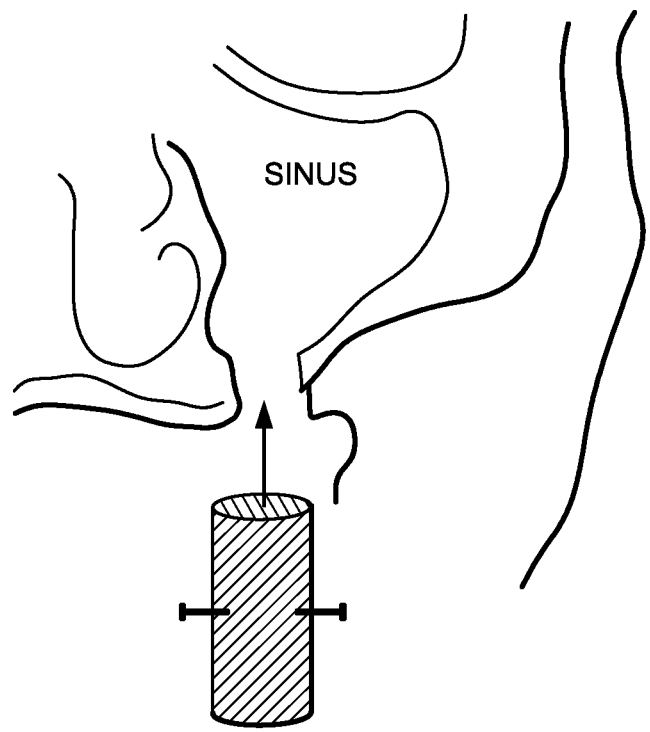
FIGS. 10A and 10B illustrate a way of using a bone harvested by the device of FIG. 1.
Figure 10B:
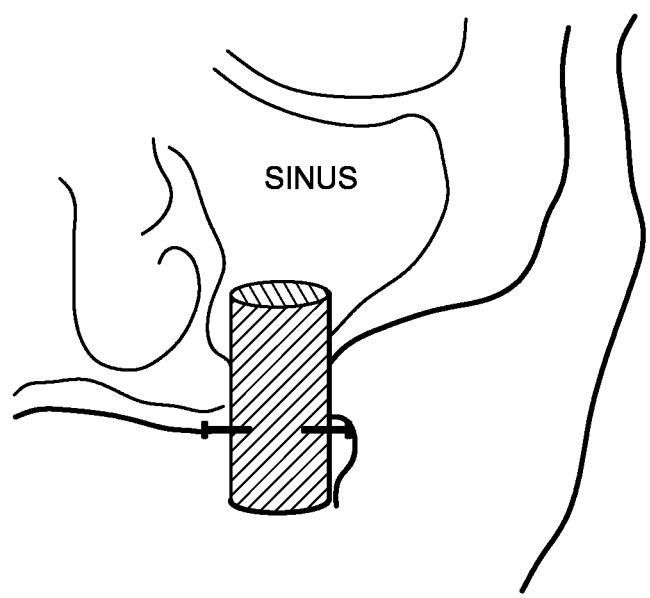

Ensuring mid-suspension may be assisted by the use of bone pins inserted at the middle of the block to act as stoppers, so that as the bone blocks are inserted into the sinus, the pins serve to limit and prevent further insertions. In this case, the pins do not actually provide any stability, but merely serve as pin stoppers, which may be left in situ, as shown in FIGS. 10A and 10B.

Figure 11:
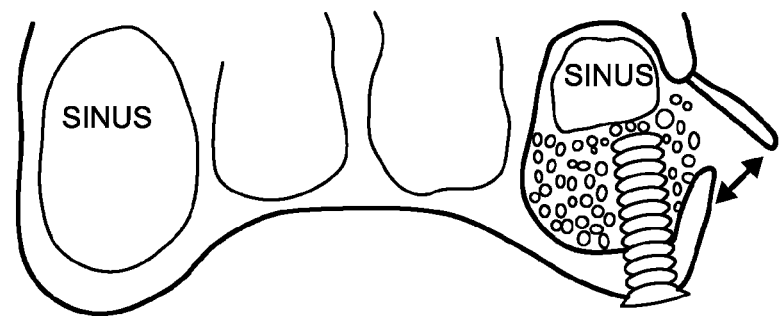
FIG. 11 illustrates the conventional open-window direct sinus lift grafting with the use of particulate bone.
Figure 12:
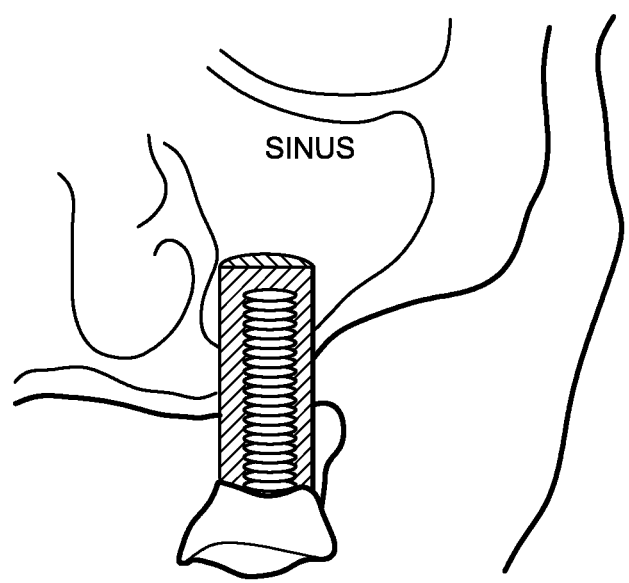
FIG. 12 demonstrates the use of an autogenous bone block harvested with the device of FIG. 1.

As the bone blocks are cylindrical in shape, these predetermined bone blocks may be procured and inserted methodically into correctly prepared drill holes. This offers an alternative sinus grafting method to the current complex sinus lift procedure. In the classic procedure involving the technique-sensitive use of bovine particulate bone mixed with saline, and as shown in FIG. 11, a large window is opened at the side bony wall of the maxillary sinus, and the thin sinus lining (Schneiderian membrane) must be carefully elevated intact, from the floor of the sinus without incurring perforations, and particulate bone material is subsequently packed to be contained underneath it. In the present invention, and as shown in FIG. 12, whole bone blocks are placed as described in the example above as a preference to the complex prior art procedure.

The key problem with the classic open sinus lift procedure is the risk of perforating the delicate and thin sinus membrane, i.e. the Schneiderian membrane, during its elevation for packing particulate bone beneath it. If perforation occurs, often the procedure is abandoned because the breach will allow free passage for the loose bone particulates to leak into the sinus to cause infections, and the loss of bone material will undermine the grafting of the dental implant, leading to its imminent failure. In contrast, with the use of the device 10 of the present invention, solid bone blocks (whether containing dental implants or not), can be inserted into the sinus with or without perforation of the sinus membrane; either perforating or lifting it respectively; in either events with no untoward consequences to the health of the maxillary sinus and thus leading to the equal successes of both final outcomes. This bypasses and quashes the fear of perforating the membrane.

However, one may reduce risking perforation of the sinus membrane by first loosening and relieving its attachment to the sinus floor with the use of a standard sinus elevation instrument in the conventional manner via the prepared hole, as shown in FIGS. 36A and 36B, prior to insertion of the bone block. In this way the sinus membrane (Schneiderian membrane) will be flabby and ready to receive the graft and to overlay it. Scientific studies have shown that maxillary sinus floor augmentation using autogenous corticocancellous block bone grafts, when installed simultaneously with the implant, is superior to autogenous corticocancellous particulate bone grafts for bone healing around dental implants. The problem has always rested on the difficulty of actually obtaining suitable blocks of autogenous bone. This problem is now solved by the use of the device 10 of the present invention, in that it can readily provide cylindrical bone blocks, and the subsequent congruous tight-fit of these anatomical bone blocks into suitably prepared holes at chosen recipient sites. This method may also provide for effective repair of oro-antral fistulas, i.e. perforations into the sinus thus creating a communication with the oral cavity, subsequent to an upper molar tooth extraction in instances where the natural tooth-roots had penetrated into the maxillary sinus. The use of bone blocks for this repair has been shown to be beneficial, and likely because it most effectively plugs the defect, as shown is FIGS. 30A and 30B.

Scientific studies have shown that it is with this congruous fit of bone blocks at the recipient site established that success is attained despite the thinness of the native bone of the deficient ridge. The condition allows dental implants to be placed immediately into each bone block, prior to insertion and integration with the deficient ridge, because the primary stability that it provides enhances success, as reported by the scientific studies.

In light of this, one may pre-insert each dental implant immediately into each harvested bone block prior to the grafting and set-up the two entities in unity for the one healing phase, and enjoy the expedient healing of autogenous bone.

In contrast, the use of particulate bone grafts does not provide primary stability for the dental implant, and if the native bone is too thin to provide stability, the insertion of dental implants will be delayed until after the particulate graft had consolidated. A delayed period of seven to twelve months may be typical of the conventional use of non-autogenous particulate grafts.

As we can see, the device 10 according to this invention enables practitioners to overcome the current problems associated with sinus grafting; namely the perforation of the sinus membrane, and the delayed placement of dental implants into unfavorably thin native bone of the sinus ridge. One may also immediately gently tap-in two dental implants of suitable dimensions into the two lower sockets previously created by the harvesting process, for the already required replacements of both of the previously missing lower first molar teeth.

With the use of the device 10 of this invention, one single operation can simultaneously solve two problems without the need for any third site unnecessary operations solely for bone donation, and eliminates the need for artificial bone material.

Autogenous bone also saves time for the patients and carries far less risks associated with foreign bone, such as Mad Cow Disease, HIV, Hepatitis B and Hepatitis C, and is readily accepted by patients who have doubts or personal or religious objections to foreign bone.

Figure 13:
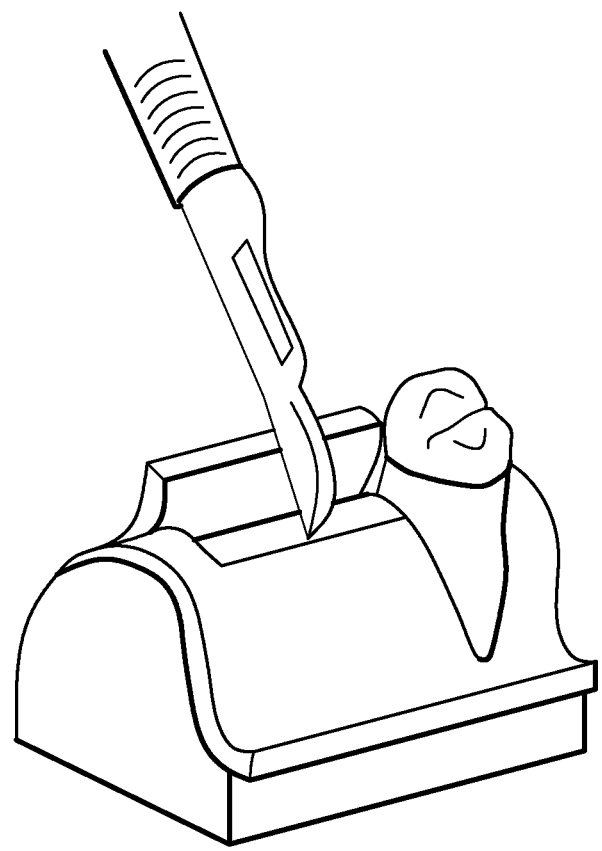
FIGS. 13 to 15 illustrate a new surgical procedure of harvesting bone from the top of the gums by using the device of FIG. 1.
Figure 14:
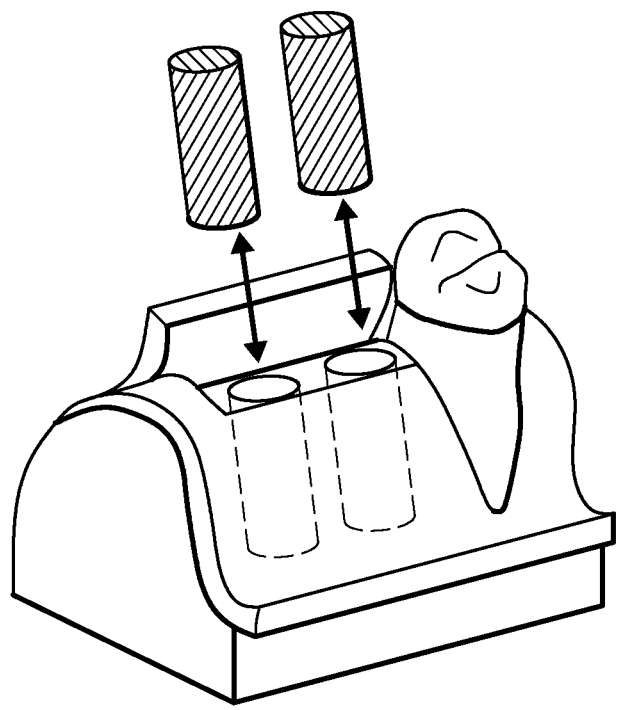
Figure 15:
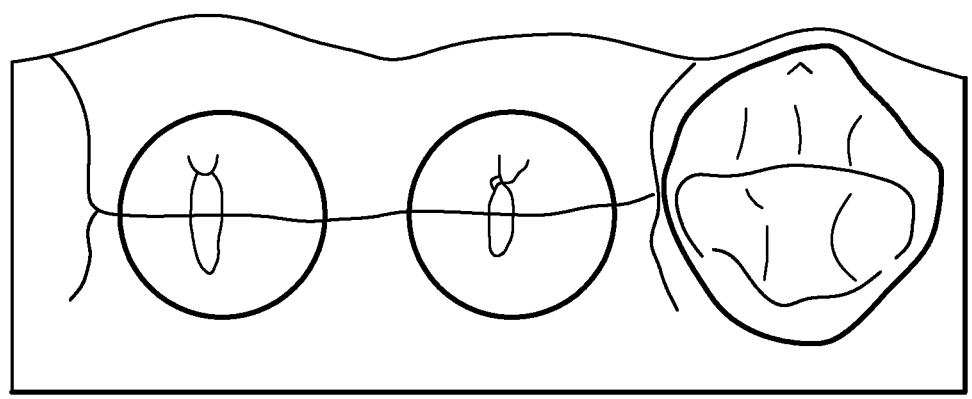

FIGS. 13 to 15 illustrate a new surgical procedure of harvesting bone from the top of the gums by using the device 10 of FIG. 1. As shown in FIG. 13, an incision is made at the top of the gum, right at the top of the ridge of a donor site (typically with use of a No.15 surgical blade) to expose the underlying top ridge, or crest of the bare bone. The device 10 is then drilled into the bone until the ring 12 contacts the top ridge of the bone. This lifts the ring 12 out of the A Position. For this to materialize, the roof of the drill cavity 38 is arranged to be higher than the bottom edge rim of the ring 12 when the ring 12 is in the A Position, so that the ring 12 contacts the bone ridge first. As the ring 12 is now activated by the spring 28 to rotate anti-clockwise (when viewed from above) towards the B Position, the drill body 36 is constantly rotating clockwise, but remaining at this depth level in the jawbone. At the same time, the saw 30 is sawing the base of the bone stud.

With the spring-loaded saw 30 now with its teeth exerting a constant and continual transverse force against the cylindrical block of bone, towards its central axis L-L, continual rotation of the drill body 36, without any further downward force exerted by the operator's hand, the base end of this cylindrical block of bone is being sawed off by the saw 30. During the rotation of the drill body 36, the saw 30 is effectively dragged into rotation to horizontally cut the base of the bone stump created by the drill body 36. The saw 30 is hinged around the central longitudinal axis M-M of the rod 40 where it makes a 90° connection to it, at its base end. The saw 30 swivels in and out of the drill cavity 38 near the end of the drill body 36, i.e. near the drill opening, and this swiveling rotation is controlled by the wheel 18 at the top of the rod 40.

Once the inner end of the cylindrical block of bone is completely sawed off, the operator can feel the sudden drop in resistance as the drill body 36 rotates more freely. As the saw 30 has now cut across the cavity 38 and lies underneath the block of bone thus cut off, it supports the block of bone and forms a floor, containing the bone block completely and securely within the cavity 36. The drilling may then stop.

As shown in FIG. 14, sockets are created and the device 10 is removed from the jaw and out of the mouth, and onto a sterile surface, for collection of the blocks of bone. As shown in FIG. 15, the gum can now be closed with a suture, to cover the jaw socket thus created. Alternatively a suitable dental implant may be gently tapped into this socket, and as the fit is perfect, suturing is optional.

The procedure described above may also be used for obtaining cylindrical bone blocks from the top of the hips, i.e. at the iliac crest; except that no dental implants will be inserted into the socket of the hips created in the harvesting process, but that the hip socket will be covered and closed with sutures for its healing.

New bone will completely regenerate within the socket after three months, to the brim. In orthopaedic surgery, because cylindrical shapes of bone blocks are essentially required for grafting, such shaped blocks can be also harvested from top of the iliac crest with the use of the device 10 of this invention. As shown in FIG. 28, currently available polymer-based bone graft substitutes in solid block forms of such exact shapes as may be harvested with the device 10 of this invention, as indicated by the letters A, B, C, D and E in FIG. 28, are produced by Orthovita, Inc., such as Cortoss and Rhakoss, as a direct consequence of the difficulties associated with harvesting autogenous bone from the body.

Bone graft substitutes can never supersede autogenous bone because their results are less predictable, and require a significantly longer time for fusion with the native bone. With references to FIGS. 16 to 21, the procedure for harvesting bone from the iliac crest will be described.

Figure 16:
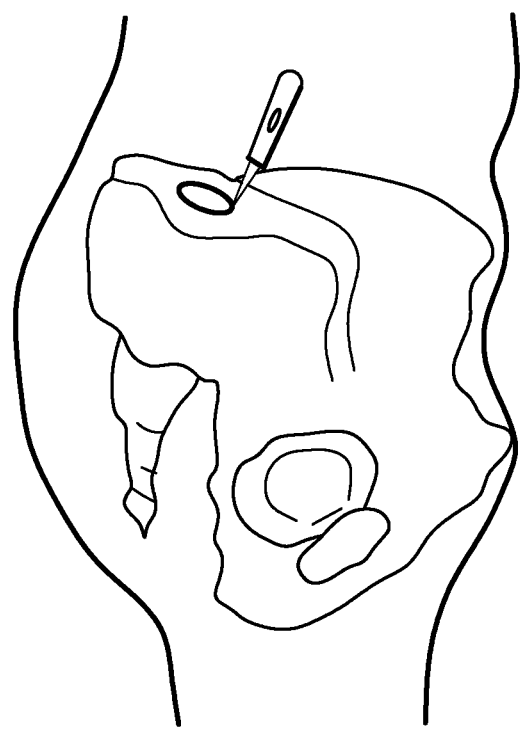
FIGS. 16 to 21 illustrate a new surgical procedure of harvesting bone from the top of the iliac crest by using the device of FIG. 1.
Figure 17:
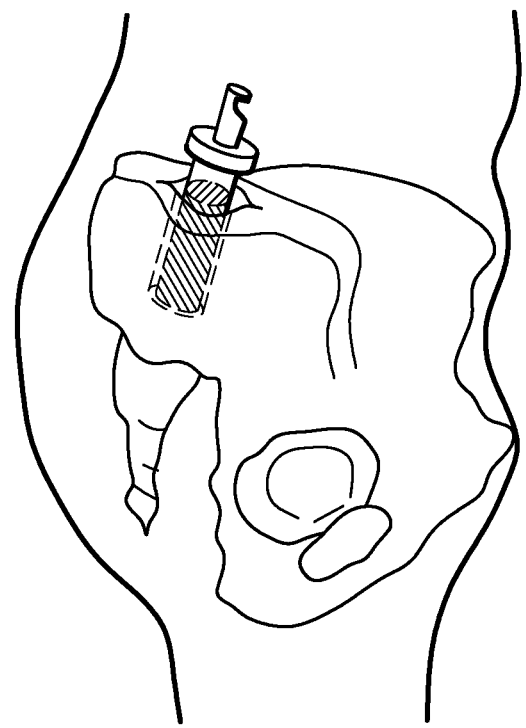
Figure 46A:
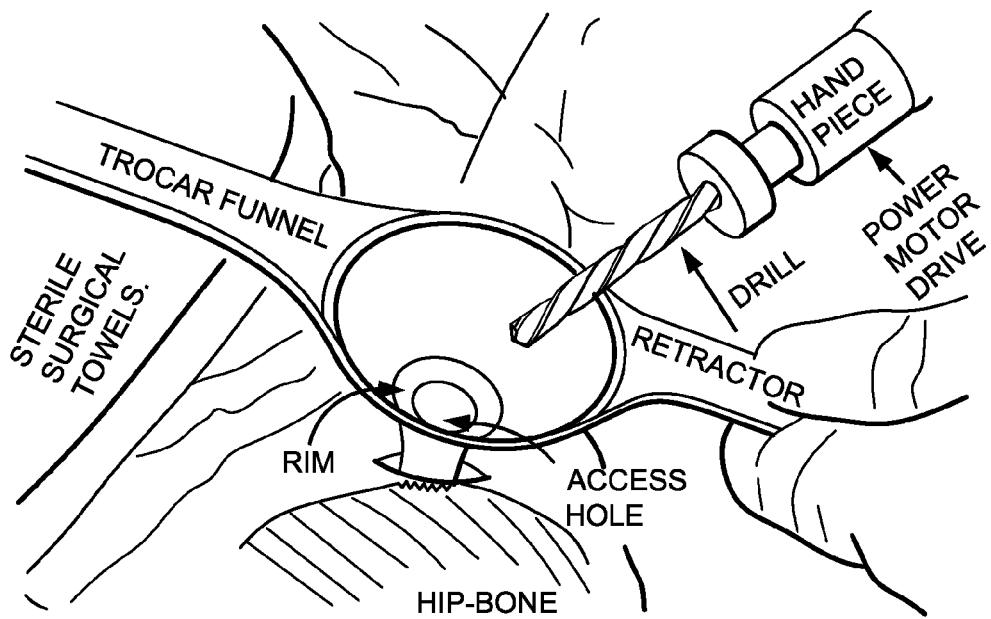
FIGS. 46A and 46B show use of the device of FIG. 1 in harvesting a block of bone from the iliac crest bone.
Figure 46B:
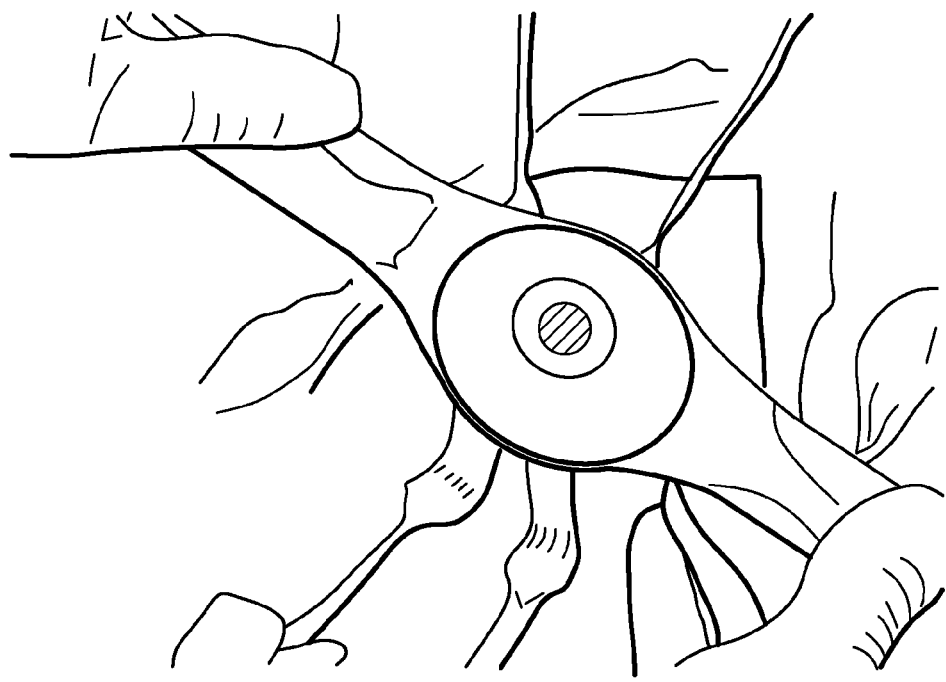

FIG. 16 shows that a scalpel first pierces the skin overlying the top of the iliac crest and penetrates through the underlying muscular fascia until it contacts the iliac crestal bone ridge. A fine line incision, avoiding major nerve structures, e.g. of no more than an inch, is then made along the superior border of the iliac crest to expose the underlying bare bone. The length of this incision is approximate equal to the intended diameter of the bone block to be harvested. This is known as a small stab incision, and the incision opening is merely required to allow access for the drill device 10 to penetrate through the soft tissues and directly into the underlying bone. The device 10, now attached to a suitable hand piece, is introduced through the slit created by this incision and into the iliac crest bone immediately below. This is in practice done via a handheld funnel-shaped trocar retractor (a funnel-shaped winged position), as shown in FIGS. 46A and 46B, which is used as an aid in obtaining proper axial inclination and stability and ensuring a pathway to the cortex of the iliac crest. The trocar funnel retractor is introduced through the stab incision with a serrated edge designed to engage the fascia and the periosteum (the top of the hip bone), thus protecting the surrounding soft tissues. In this case, the ring 12 is to be activated (i.e. lifted out of the A Position) at the instant the bottom of the ring 12 contacts the top of the immediate rim around the funnel hole, when the device 10 is introduced deep into the bone to an appropriate depth. As further deeper penetration is restricted by the ring 12 abutting the rim of the funnel above the funnel hole, further rotation of the drill body 36 will only bring about severing of the bottom of the block of bone captured within the cavity 38 of the drill body 36. In this hip-bone scenario, the ring 12 and the wheel 18 may each be of a wider diameter, as in contrast to the situation for operation in the jaws in which the presence of neighbouring teeth may limit access to the done site. Of course, the tips of neighbouring teeth may be used for activating the ring 12, in which case this has to be taken into account when considering the effective length of the drill body 36.

The harvesting procedure is then carried out by the device 10 in the same fashion as discussed above, and as shown in FIG. 17.

Figure 18:
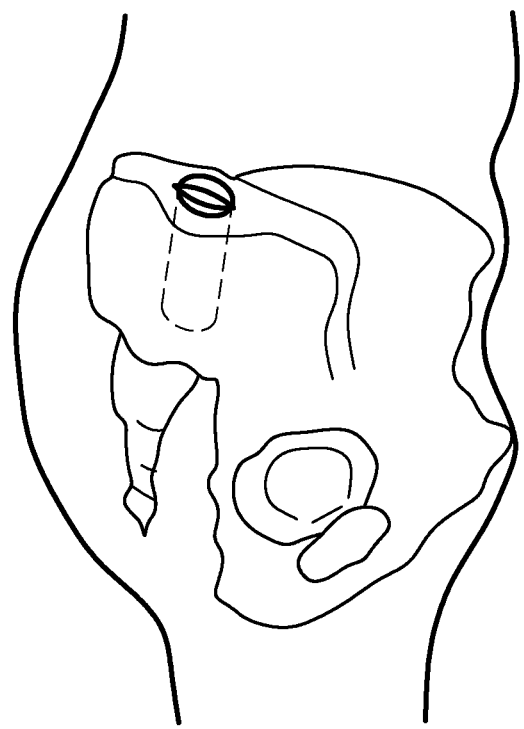
Figure 19:
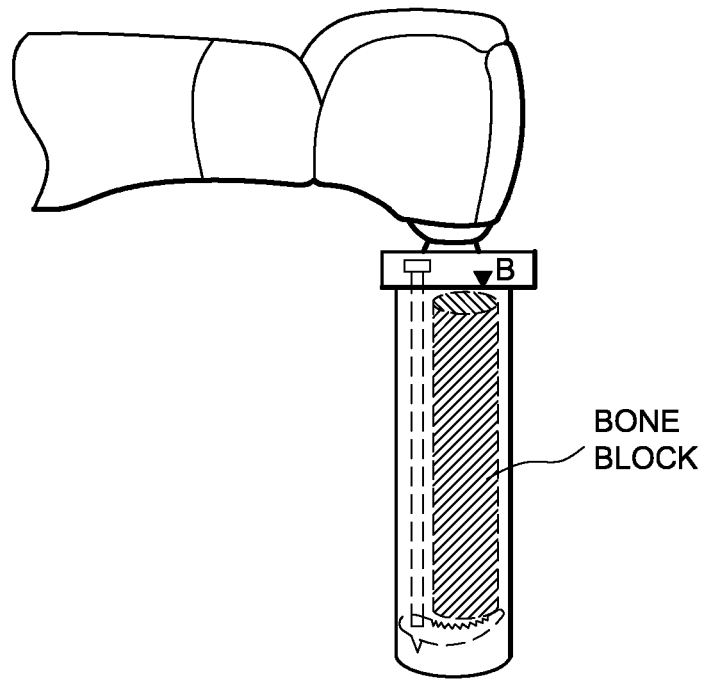
Figure 20:
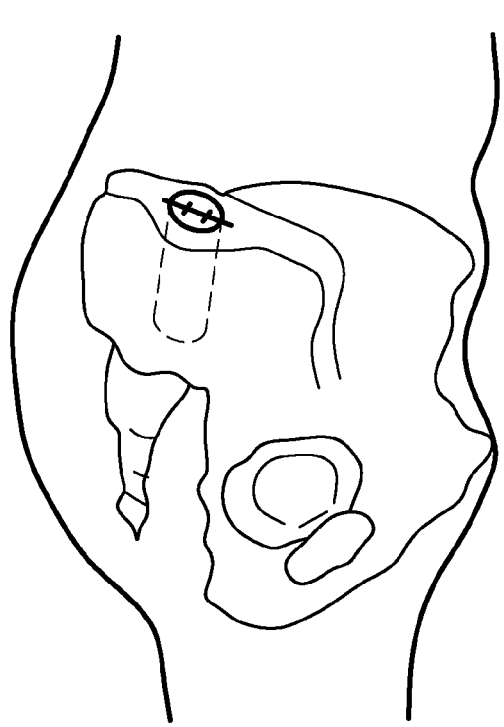
Figure 21:
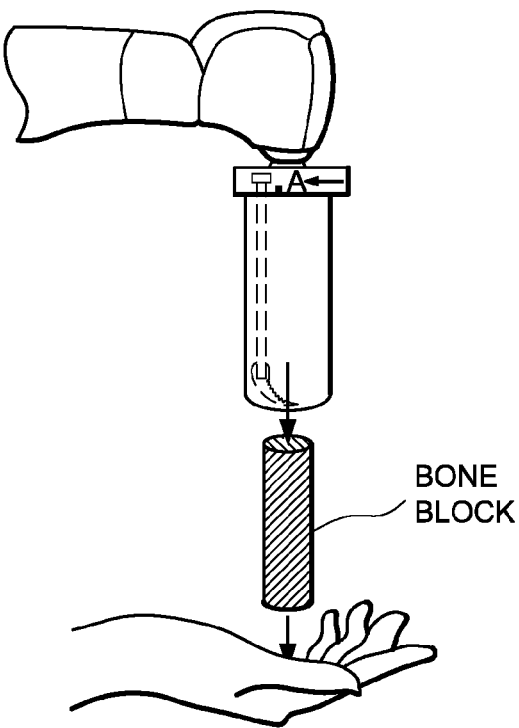

FIG. 18 shows the socket created in the iliac bone, and FIG. 19 shows that the block of bone is within the device 10 now outside of the body. FIG. 20 shows that the overlying soft tissues have been sutured, and FIG. 21 shows release of the block of bone from the drill cavity 38 of the device 10. After harvesting the bone graft from the iliac crest, bone wax or gelfoam may be carefully and evenly compressed with the finger and a sponge (4×4) into the iliac socket created and interstices of the remaining cancellous bone. This will prevent post-operative haematoma formation. Great care is taken to remove all loose pieces of bone and bone wax which can act as foreign bodies, and the wound is closed in the usual fashion.

Please also note that the length of the cylindrical bone block is limited by the ring 12 at its upper end and the roof of the drill cavity 38, and is limited at the lower end by the upper surface of the saw 30. The diameter of the bone block is determined by the internal diameter of the inner cutting surface of the drill body 36.

The present invention provides completion to the whole mission, as the existence of a suitable saw is hereby well-positioned at the right time and the right place to effectively severe the soft cancellous bone at the base of the bone stud, which is otherwise a difficult area to access and compromise. Large bone studs would leave the operator bewildered, and this is currently avoided with the use of the current bare trephine drill. By the use of the device 10, a further method to harvest more bone is to look for those diseased teeth, retained roots, and wisdom teeth which are already planned for extractions, the processes of which create extraction sockets. In such cases, all of these teeth are first extracted, and the patient returns after three months when new socket bones have regenerated and refilled these sockets to the brim. The device 10 is applied to harvest such socket bone collectively, and the new sockets created are either left alone to heal, or are to receive dental implants immediately. In the latter way, autogenous bone is obtained from intraoral sites of the jaws which are already in need of refurnishment with dental implants, and during the process of their preparation for receiving dental implants, the bone which is necessarily drilled for implant purpose is now collected with the device 10 for its new purpose, i.e. as an autogenous bone block for grafting. In essence, the present invention allows those intraoral sites already in need of dental implants to become the donor sites of bone procurement.

Figure 22:
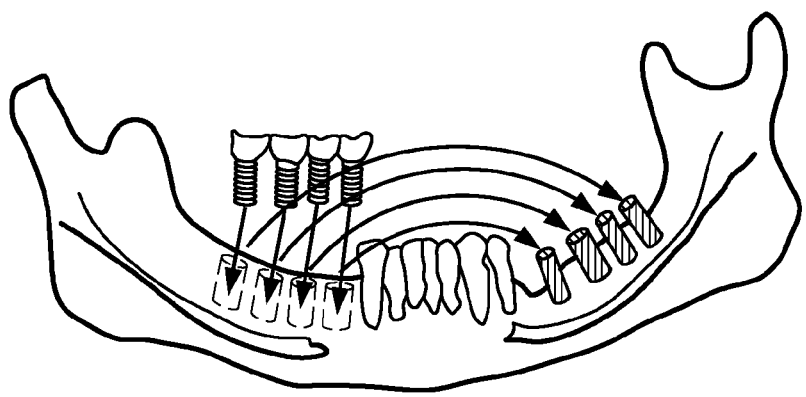
FIG. 22 illustrates a new method of harvesting bone blocks and to immediately replenish the prepared sockets of the donor site with exactly matching dental implants, by using the device of FIG. 1.
Figure 23:
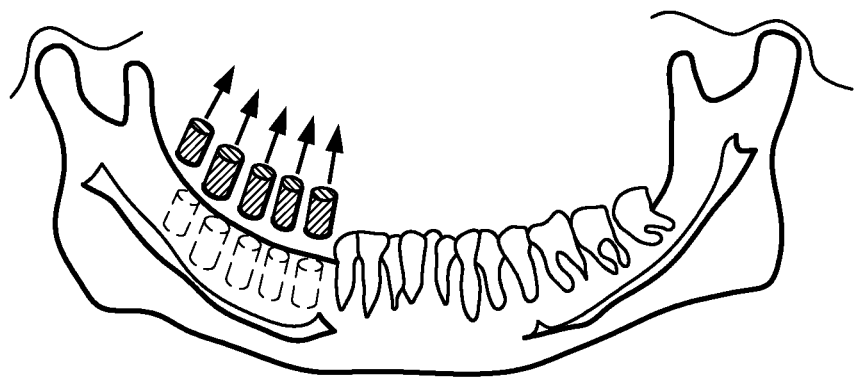
FIG. 23 illustrates bone blocks harvested from the top of the gums, such being socket bone, or new bone which has regenerated into the empty sockets subsequent to teeth extractions.

FIG. 22 illustrates how bone blocks are first harvested and then transported across the mouth from one site to another, for grafting, followed by the immediate insertion of dental implants into the voids, or sockets, thus created. Previously, one would have thought that a second operation site required for harvesting autogenous bone was the prime disadvantage. The present invention now takes advantage of those other needs in the intraoral sites of the jaws and provides a one-step solution which compliments the two problems simultaneously. In this way, no unnecessary operation is carried out, and the donor sites with the new implants and recipient sites with the grafted bone are both set for the healing phase at the same time. FIG. 23 illustrates bone blocks harvested from the top of the gums, such being socket bone, or new bone which had regenerated into the empty sockets subsequent to teeth extractions.

Figure 24:
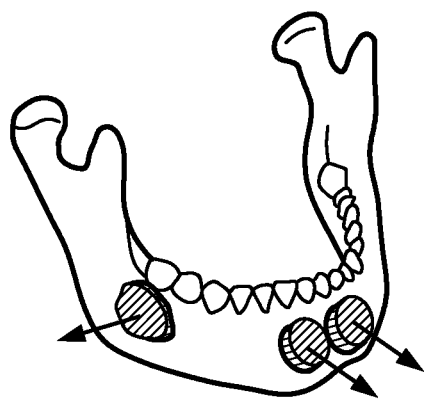
FIG. 24 illustrates bone blocks harvested by the device of FIG. 1 from the outside of the jaw, genial region and buccal shelf.

The device 10 according to this invention can be used for removing a precise cylindrical block of the patient's bone conservatively from any area in the jaws, including the top of the gums (as shown in FIG. 22), or the outside of the jaws (as shown in FIG. 24). In particular, in addition to harvesting bone from the top of the gums, the device 10 may harvest bone from the side of the jawbone, as from the genial region and buccal shelf areas, as shown in FIG. 24. In this latter case, the circular bone blocks will be of large diameters and relatively thin. Currently this is practiced with the ordinary trephine bone drill, prior to manual procurement of shallow bone blocks with the use of cumbersome elevators. The advantage of the present invention is that it automatically provides procurement, and delivers the block in full containment.

Figure 25:
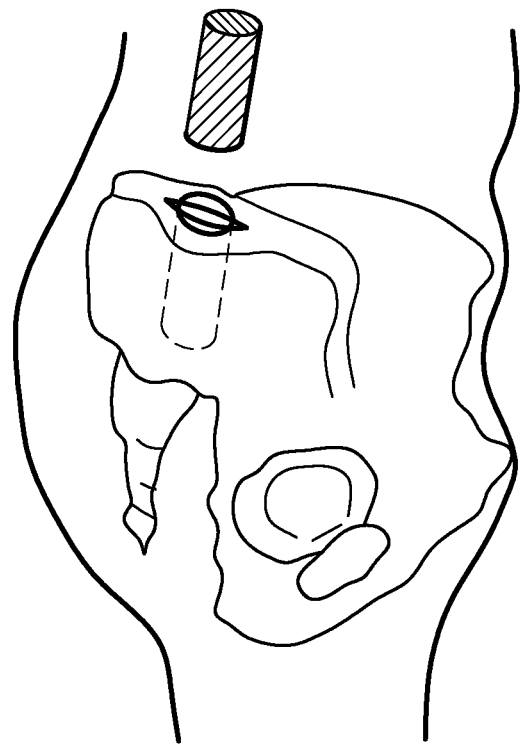
FIG. 25 illustrates a bone block harvested from the iliac crest by the device of FIG. 1.

FIG. 25 illustrates a bone block harvested from the iliac crest by the device 10 according to this invention.

Figure 26:
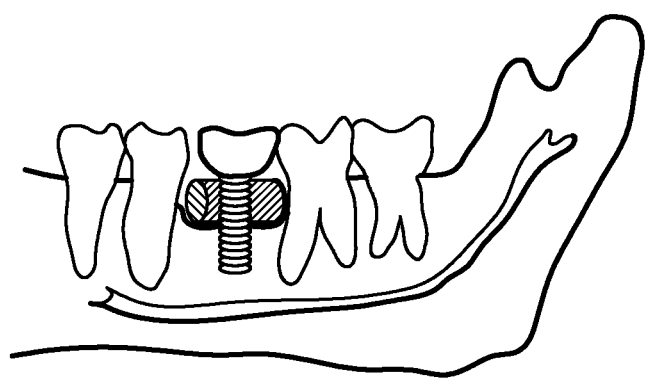
FIG. 26 illustrates a vertical ridge grafting with a block of bone harvested by the device of FIG. 1.
Figure 29A:
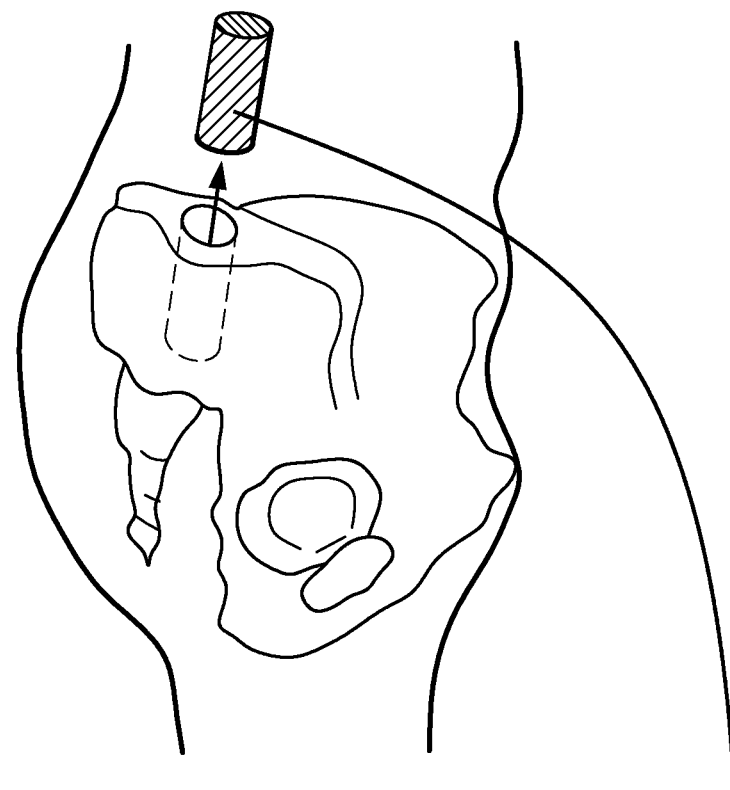
Figure 29B:
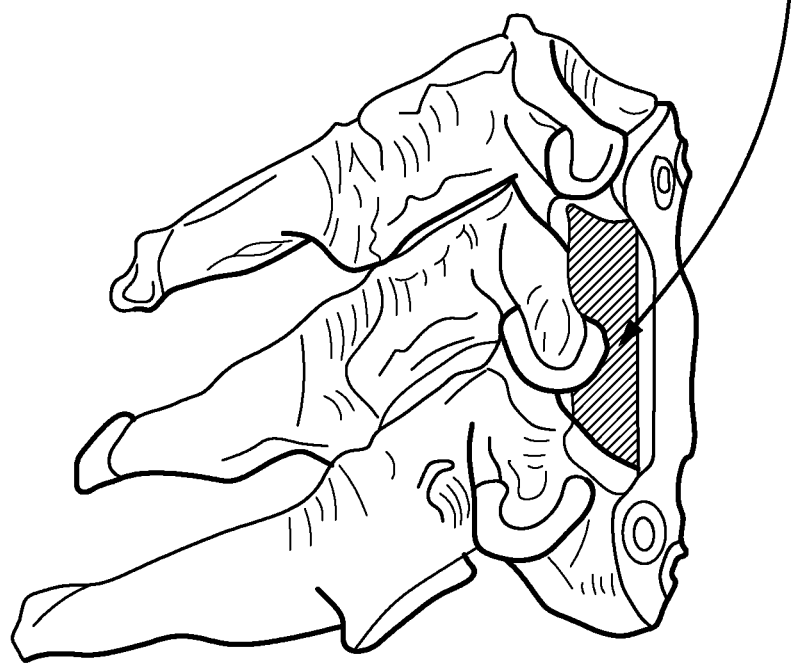
Figure 30A:
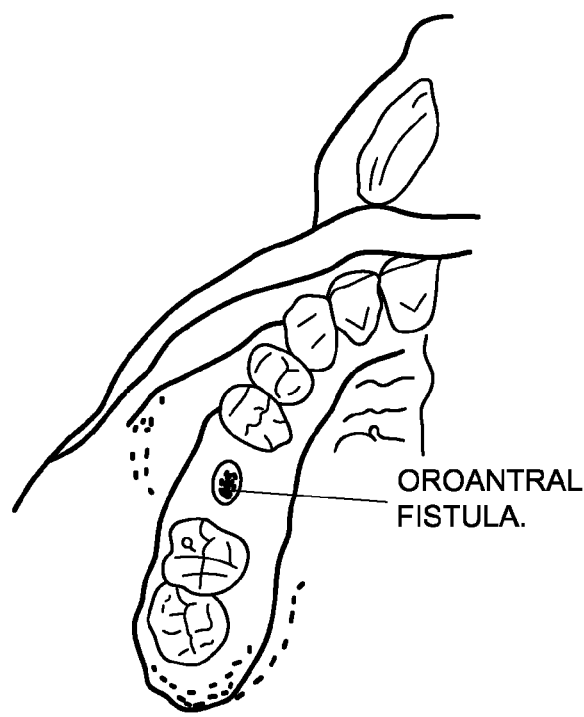
FIGS. 30A and 30B illustrate the use of a bone block for the repair of an oroantral fistula; upper right molar area.
Figure 30B:
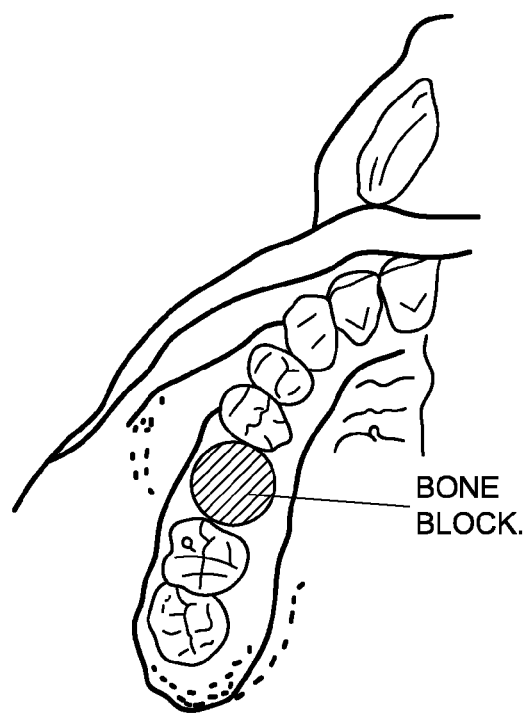
Figure 31:
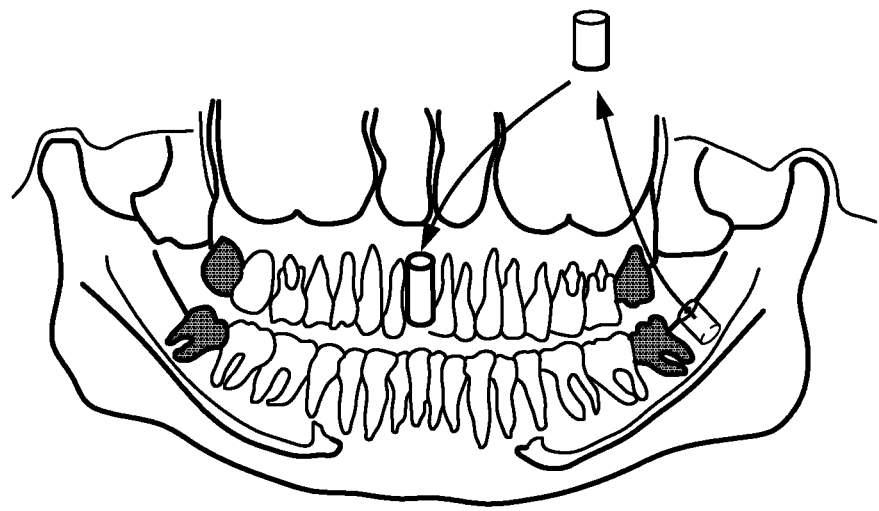
FIGS. 31 to 33 illustrate an example of bone block grafting for an extraction socket.
Figure 32:
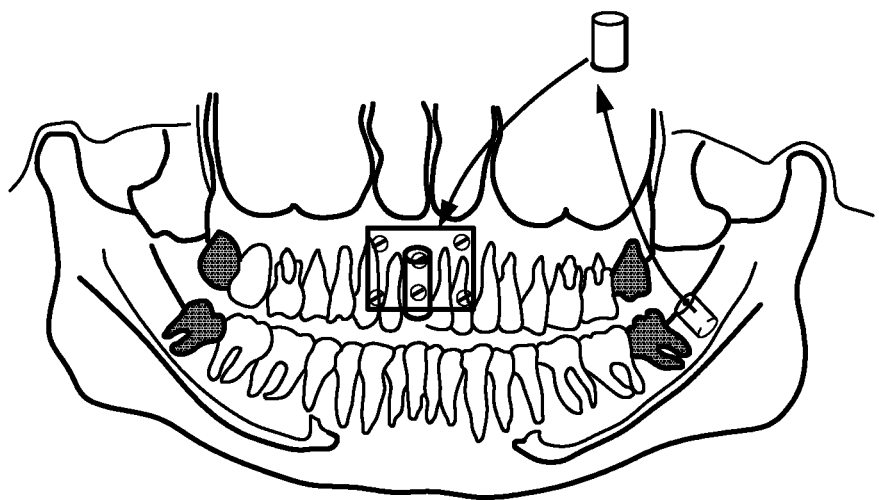
Figure 33:
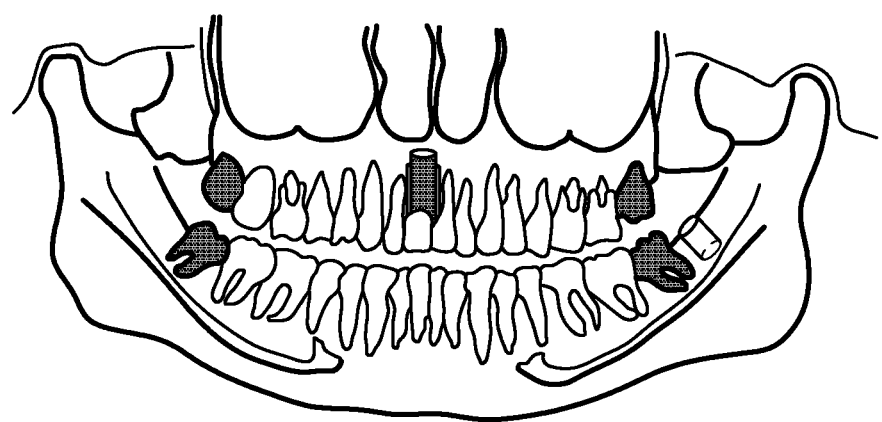

Once a block of bone is obtained by this device 10, such can be used for various grafting procedures. It can be crushed into fine or coarse particulates to be used as filler particulates suitable for grafting:

1. bone loss around natural teeth, as in gum disease;
2. bone loss around failing dental implants, as in an implant dehiscence. However, bone blocks are more tangible and superior to bone particulates for bulk bone grafting;
3. vertical ridge grafting (to increase the vertical height of the low ridge), as shown in FIG. 26. This is an important application provided by the device 10 of this invention, as the block of bone can be used to replace the use of a well-known prior art procedure called distraction osteogenesis and its cumbersome device, for the purpose of increasing the vertical ridge height. In this prior art method, the upper bone portion of the deficient ridge is separated from the underlying bone portion, and both bone segments are attached to a surgically placed screw-opening device with which the patient unscrews every three days, for incrementally increasing the gap between them. Bone is expected to regenerate within the increasing gap. The established technique takes advantage of the development of bone that results when an osteotomized segment of bone is moved, new bone formation occurs within the gap. Distraction osteogenesis has many disadvantages; it is openly invasive, involves higher complications, the device is precarious and uncomfortable in the mouth, very complex to surgically place, requires the patient's stringent compliance to operate it dexterously in the mouth regularly, to keep it clean as it is prone to infections. It is a slow and tedious process, and the device is required to be surgically removed afterwards;
4. horizontal and lateral ridge grafting (to increase the thickness of the ridge), as shown in FIGS. 27A and 27B;
5. sinus grafting procedure - to insert a block of bone through the floor of the sinus in a congruous fitting fashion for supporting dental implants. This provides adequate bone block stability, obviates the need for additional bone pins and screws, and side-steps the need for an open sinus lift;
6. spinal fusion in orthopaedic surgery. A cylindrical bone block of a suitable size may be harvested from the iliac crest with the device 10 of this invention for spinal fusion surgery, as shown in FIGS. 29A and 29B;
7. an extraction socket, with defective bone conditions, as shown in FIGS. 31 to 33. A bone block is retrieved from behind the wisdom tooth and placed onto the prepared site of the upper front missing tooth's deficient socket (FIG. 31). The bone block is then fixed onto the socket by means of pins or screws and is covered by a titanium membrane, sutured and the site is allowed to heal for three months, as shown in FIG. 32. Afterwards, an appropriate dental implant is placed into the graft and a crown is provided (as shown in FIG. 33), and especially for an oral-antral fistula (OAF), as shown in FIGS. 30A and 30B.

A unique feature of this invention is that the device 10 can remove bone blocks in such an exact fashion that the sockets created in the process will completely heal, henceforth allowing continual repeatable harvesting of the bone blocks at three-month intervals, if required. This process is made possible by the fact that the cortical plates of the jaws are not breached during the harvesting procedure using the device 10 of this invention.

As new bone will regenerate between intact cortical bone plates within a socket, this provides an unlimited supply of autogenous bone for bone grafting procedures, and this invention offers a conservative surgical approach for this purpose, over prior art.

If the sockets are allowed to heal completely, all the bone harvested will regenerate and will leave neither permanent damage nor disfigurement at the donor sites, leaving no traces of evidence of all previous events on a radiograph taken after three months.

Figure 34:
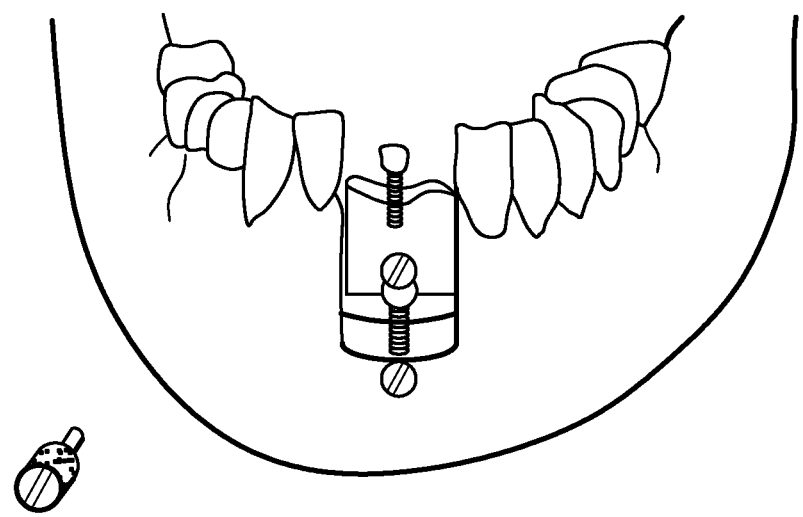
FIG. 34 illustrates a process known as distraction osteogenesis.

Pathologically speaking, there are only two main ways to potentiate full bone regeneration. The first way is to create intact sockets which become nests for new bone, known as socket bone. The other way is to split and separate the osteotomized segments of bone for new bone to form within the gap, a process known as distraction osteogenesis, as shown in FIG. 34. This invention focuses on the former way, and the block of bone collected may be utilized for many purposes, including the use of distraction osteogenesis, superseding the latter way, as illustrated in FIG. 35.

Figure 37:
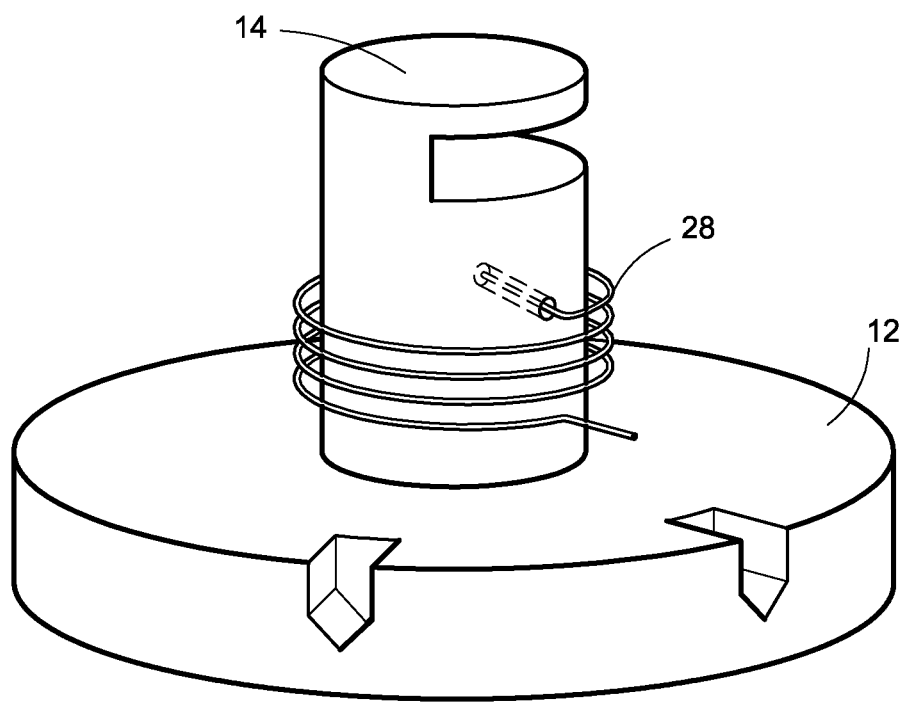
FIG. 37 shows an alternative arrangement of the spring of the device of FIG. 1.

Further modifications and improvements may be made to the present invention. For example, as shown in FIG. 37, the spring 28 may be wound around the drill shaft 14, so as to increase the biasing force which drives the actuation ring 12 from the A Position to the B Position.

Figure 38:
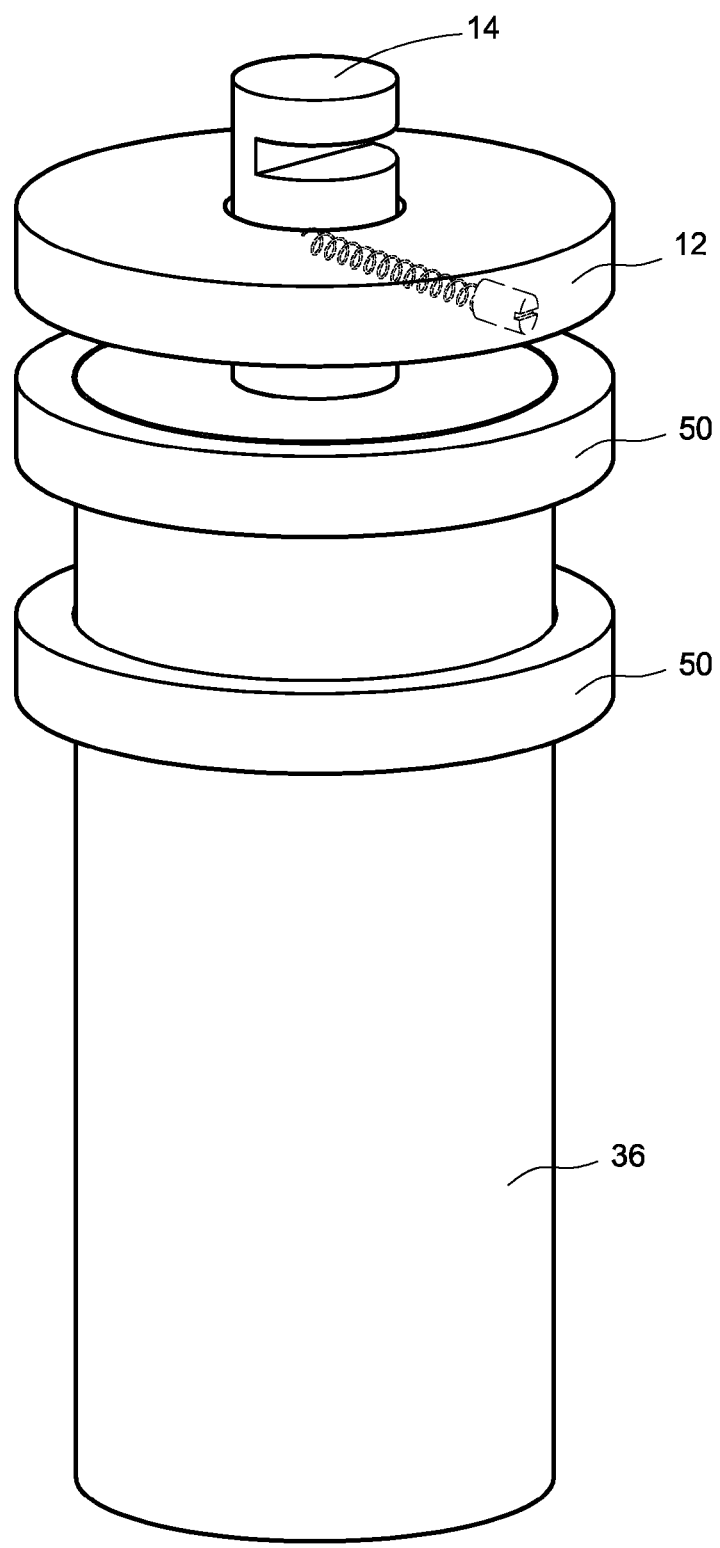
FIG. 38 shows an accessory ring which may be used in conjunction with the device of FIG. 1.

Additionally, one might consider providing at least one calibration ring 50 of a thickness of, e.g. 1 mm. The calibration ring 50 can be screwed onto the bottom of the actuation ring 12 so that it can touch the crest of the bone 1 mm sooner, and hence prematurely triggers the saw 30 earlier for sawing out a shorter block. As the drill body 36 may be fabricated to only specific lengths of perhaps even numbers of 6 mm, 8 mm, 10 mm or 12 mm, the calibration rings 50 can be provided to help make a calibration for reduced odd numbers of 5 mm, 7 mm, 9 mm, 11 mm respectively, or even added collectively onto each other to further effectively reduce and alter a given limited available drill choice available at the time in the surgery room, as shown in FIG. 38.

Figure 39:
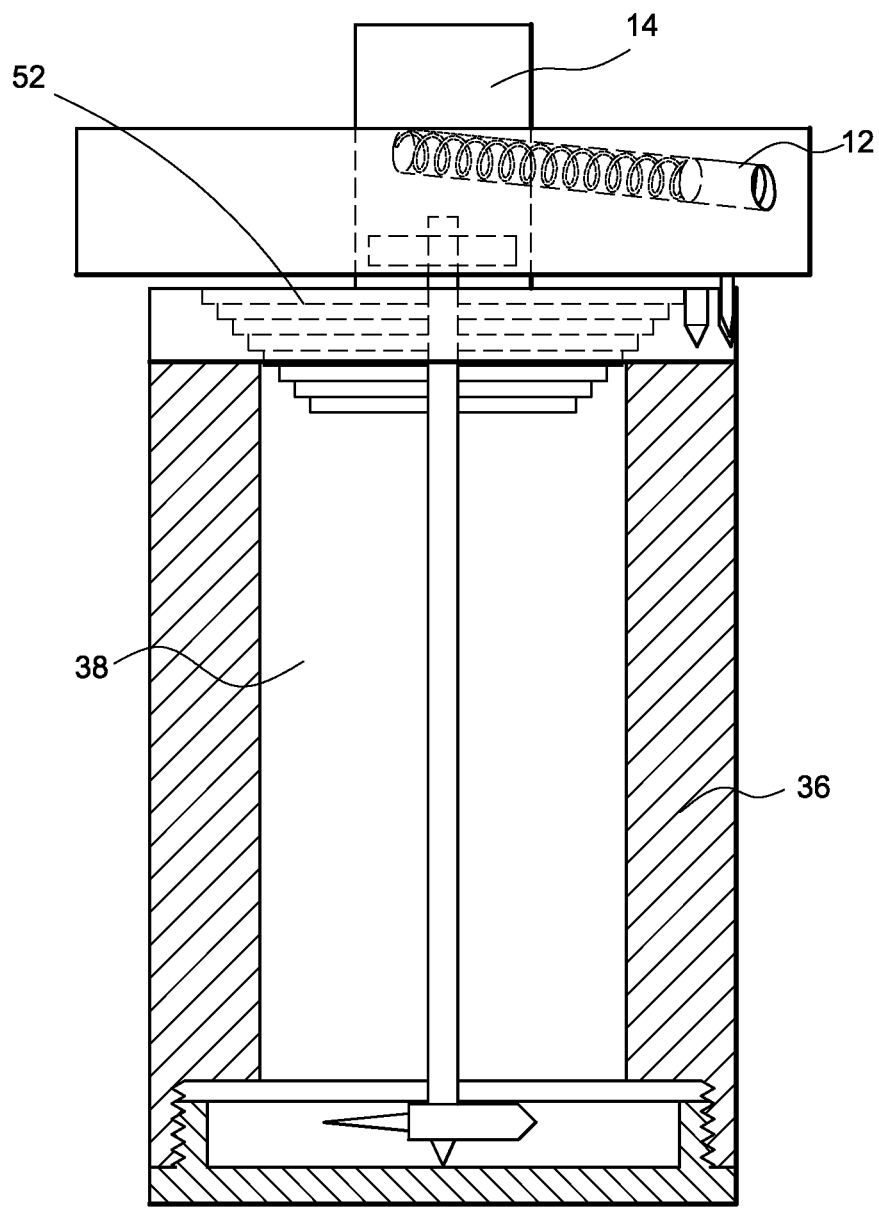
FIG. 39 shows an alternative arrangement between the drill shaft and the drill body of the device of FIG. 1.
Figure 40A:
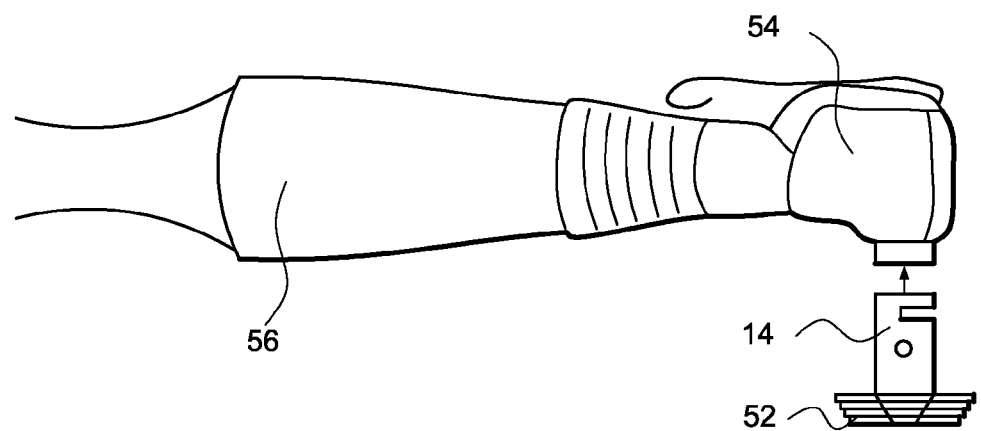
FIGS. 40A and 40B show two hand pieces to which the device shown in FIG. 39 may be releasably attached.
Figure 40B:
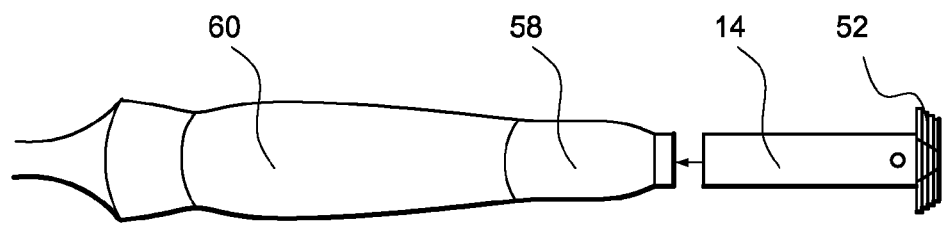

An optional screw-threading connection of the drill shaft 14 to the drill body 36 may be provided, as shown in FIG. 39. In this arrangement, the drill shaft 14 is releasably engageable with the drill body 36 threadedly via a connection lid 52. This arrangement allows other forms of drill shafts (such as the common latched-grip or friction-grip types) as corresponding to different hand pieces (whether angulated or straight types) to be interchangeably used, as preferred by different operators, as suitable for usage at different areas of the body (such as the jaws or the hips). As shown in FIG. 40A, the drill shaft 14 with the connection lid 52 may be releasably attached to a latch grip head 54 of an angulated hand piece 56. As shown in FIG. 40B, the drill shaft 14 with the connection lid 52 may be releasably attached to a friction grip head 58 of a straight hand piece 60. The connection lid 52 may be made to a suitable width, comparable to that of the drill cavity 38, so as to provide an optional accessory opening, allowing delivery of the harvested block of bone from this top end of the drill body 36. The drill shaft 14 also serves as an opening lid for the exit of the bone block, at the top of the drill body 36, and thus the drill shaft 14 doubles as an exit lid in addition to serving as a variable type intermediate connector.

Figure 41A:
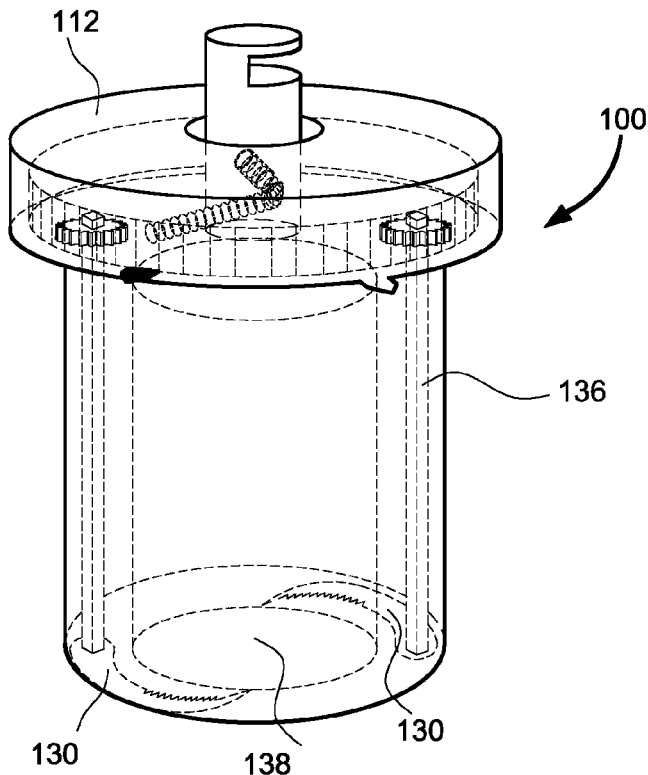
FIGS. 41A and 41B show a bone harvesting device according to a further embodiment of the present invention.
Figure 41B:
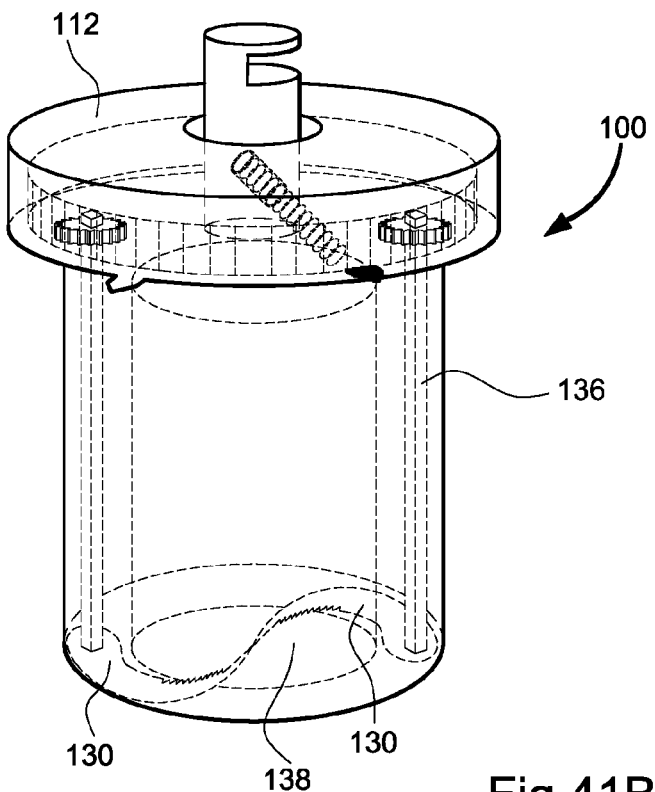

According to a further embodiment of the present invention, a bone harvesting device 100 according to this invention may incorporate two or more saws 130 (with their associated components) to increase the efficiency of the device 100 for sawing and delivering larger bone blocks out of the body, as shown in FIGS. 41A and 41B. When an actuation ring 112 of the device 100 is in the A Position, as shown in FIG. 41A, both saws 130 are hidden under the lower end of the circular wall of a drill body 136, and are thus clear of an open lower longitudinal end of a drill cavity 138 of the drill body 136. When the actuation ring 112 is allowed to rotate to the B Position, the saws 130 are swiveled to the position as shown in FIG. 41B, in which they extend into the lower open end of the drill cavity 138 of the drill body 136. The base of a block of bone to be harvested is sawed out during the swiveling movement of the saws 130.

According to a still further embodiment of the present invention, and as shown in FIGS. 45A to 45D, a bone harvesting device 200 according to this invention may incorporate a coil spring 262. In particular, an end of the coil spring 262 is fixed to an inner surface 264 of a drill shoulder 216, and another end of the coil spring 262 extends into a drill cavity 238 of a drill body 236. During drilling, a bone block 266 is received into the drill cavity 238. The coil spring 262 acts on and biases the bone block 266 away from the drill cavity 238 and the drill shoulder 216. When a saw 230 is moved from the position as shown in FIGS. 45C and 45D to the position as shown in FIGS. 45A and 45B, the coil spring 262 ejects the bone block 266 from the drill body 236, thus facilitating retrieval of the bone block 266 from the device 200.

It can be seen from the foregoing discussion and the accompanying drawings that a device 10, 100, 200 according to this invention is also capable of removing diseased bone, e.g. bone cancers, and the bone graft that it harvests can also repair the bone loss caused by cancers, or some types of fractures.

The harvesting of a block of autogenous bone by the device 10, 100, 200 of this invention is a two-step continuous process. The first step is to drill vertically down into the bone. The diameter of the drill cavity 38, 138, 238 determines the diameter of the bone block, and the depth of drill body 36, 136, 236 determines the length of the bone block to be harvested. The second step is to proceed to saw horizontally across the bottom of the bone stud created by the first step, at the instant the drill body 36, 136, 236 has arrived at a chosen vertical depth in the bone, to conclude the final length of the bone block to be harvested. The device 10, 100, 200 of this invention achieves this two-step process in one continuous action. In the process, the second step must be at a separate and chosen moment during the procedure because the activation of this process would immediately determine the final length of the harvested bone block. The trigger of the actuation ring 12, 112, whether automatically as factory-set, or prematurely by a movement of a fingertip of the operator on the ring 12, 112, allows selection of the cut-off point. This invention provides an exact method for the harvesting process. The method involves a minimal invasion process of drilling into the bone at the donor site in exact proportion to the volume of bone required for grafting; and via a minimal incisional access opening through the soft tissues which serves both for the introduction of the drill device into the bone, and for its subsequent retrieval, containing a harvested block of bone. No extended breaches to both the soft and hard tissues is incurred at the donor site beyond the exact dimensions of the drill body 36, 136, 236, plus without the mandatory need for a direct vision during this harvesting procedure. This also opens great opportunities for general dentists to proceed with bone grafting, enabling them to readily harvest autogenous bone from their patients. Whereas an ordinary trephine bone drill can create a cylindrical stud of bone as it drills, it cannot sever the end of the stud in order to free it and also to procure it. The device 10, 100, 200 of this invention goes one step further in providing total procurement and delivery of the bone block.

The device 10, 100, 200 of this invention also provides a carrying device for use in oral surgery and orthopaedic surgery, suitable for the precise harvesting and delivering with provision of complete containment of a pre-determined volume size of a cylindrical block of autogenous bone in one continuous two-step action either from the patient's jawbone from the top of the patient's gums, or from any bone of the body skeleton, such as the pelvis or the iliac crest, for bone augmentation. It is a contraption which creates and entraps to carry a cylindrical block of bone.

This invention also increases the possibility of obtaining abundant supply of autogenous bone from intraoral sites of the jaws, encouraging its preferential usage by raising and rendering the maximal permissible capacity of the convenient jaws for self bone donation. This in turn reduces the need to resort to all other bone products, including allografts and alloplasts. This invention also aims to achieve the harvesting of the patient's own bone via the minimal necessary size incisional opening of the patient's soft tissues, for a smallest resulting wound.

This invention also aims to create a new opportunity for dentists to harvest the patient's own bone with ease and with a minimally invasive technique, and no specialist skills are required of them. The invention provides for a unique ease of use because amidst all other tools, dental and surgical operators are most familiar with their first favourite tool, namely the drill, which is powered by a standard hand piece.

It is also aimed to find a less invasive and more conservative method for attaining autogenous bone for the grafting. A minimal invasive technique for an atraumatic surgery in the quest to obtain autogenous bone with precision is the ideal. This can reduce bone wastage during the process.

This invention allows for block procurement of socket bone from intraoral sites in the jaws. Socket bone is referred to as the underlying bone located wherever there are gaps in the dentition of the jaws. It is typically dense with both the components of cortical (compact bone) as well as cancellous (spongy bone), known as cortico-cancellous bone, which is ideal for bone grafting. This approach takes advantage of the common fact that, in many cases, there are also other missing teeth where there is underlying good quality and quantity of bone suitable for harvesting, for example, missing premolars, missing wisdom teeth, and certainly the areas of bone immediately behind the wisdom teeth, in any event. Whereas these may be all good candidate donor sites for bone harvesting and the standard trephine bone drill is indeed able to carve an initial bone stud in the site, it leaves the bone stud in situ for the operator to manually procure it.

This procurement is immensely difficult and farfetched, especially when the required bone block must be large, and the stud thus created is wide, long and too deeply embedded. Proceeding to do so is currently tedious, invasive and traumatic.

A first significance of this invention is that it renders the jaws as a potentially unlimited supply of autogenous bone for intraoral site bone harvesting.

This applies in cases where the volume collection of bone blocks as described above remains inadequate to replenish all of the severely deficient sites of the jaws e.g. for the severely atrophic posterior mandible or maxilla bony ridges, then these sockets are simply allowed to heal again for a further three months for a second process of bone collection, and these are recurrently harvested and grafted onto the deficient sites of the jaws. The whole process can be repeated yet again until finally all the deficient bone areas of the jaws have been completely replenished and suitable to house all the necessary dental implants. This will provide a reasonable alternative over harvesting autogenous bone from other parts of the body (typically the pelvis or the iliac crest) with their associated morbidity.

A second significance of this invention is that it is capable of producing autogenous bone blocks of predetermined sizes, and in the most anatomic shape form suitable for human body grafting, namely, the cylindrical form. At the recipient site, slightly reduced matching circular holes can be prepared to receive for congruous fit of these cylindrical shapes of bone blocks, omitting the need of bone screws and bone pins to provide the initial stability. The stability is inherently provided by the congruous tight friction contact of the bone blocks to the native bone, at the rims of the prepared receiving holes. Maxillary sinus grafting in this way actually "invites" the immediate placement of implants into these blocks as stability is already present.

A third significance of this invention is that the sockets created in the processes of bone harvesting are already suitable for receiving dental implants. Unfortunately, the current methods of bone harvesting in orthopaedic surgery is most traumatic with the use of prior art tools, that it induces subsequent morbidity, excessive bleedings and such prolonged pain at the donor site after the operation that led to the development and pursuit of alternative artificial, non-autogenous, bone products for the cause. Such bone products also require seven to twelve months for their complete fusion with the native bone at the grafted sites as opposed to the three months required for autogenous bone, thus significantly delaying the healing phase in orthopaedics.

This invention also aims to reduce the known morbidity associated with such orthopaedic procedures in which prior art tools are used, by offering a much more atraumatic and conservative surgical approach with its minimal invasion technique which can limit the discomforts for a more uneventful healing. In this way, autogenous bone blocks can be harvested with much ease, and its use for grafting in preference to the employment of commercial bone products will be encouraged.

Figure 42:
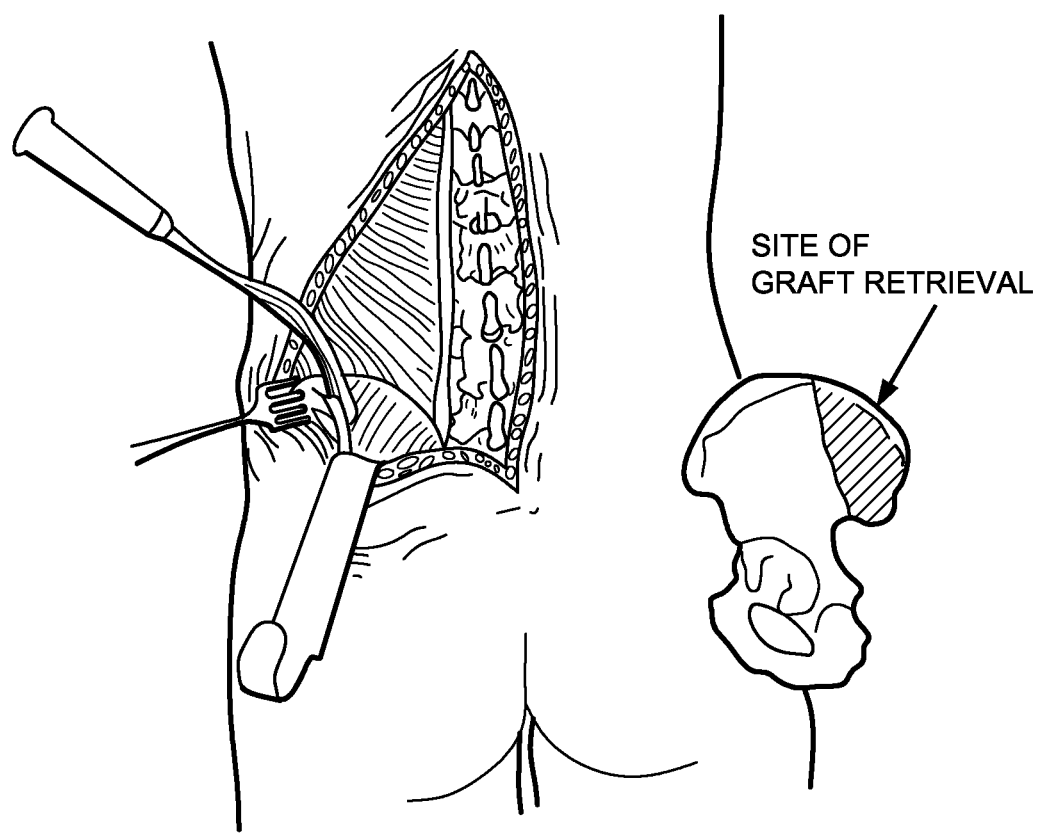
FIG. 42 shows use of bone in a conventional open reshaping process, which is a most invasive process.

The tools available today for the specialist oral surgeon to harvest bone are mostly crude and generally imprecise, relying entirely on the skill of the operator. Volumes of bone are sawed out with external rotary saws which often leave the donor sites amputated. Conventionally bone is removed with an external approach from the outside of the jawbone, breaching the outer plate of the jaws, i.e. the cortical plate; and likewise, the raw and crude harvesting of bone from the hips, i.e. the iliac crest. Subsequently, significant amounts of harvested bone are typically wasted in the conventional reshaping process, as shown in FIG. 42.

Figure 43:
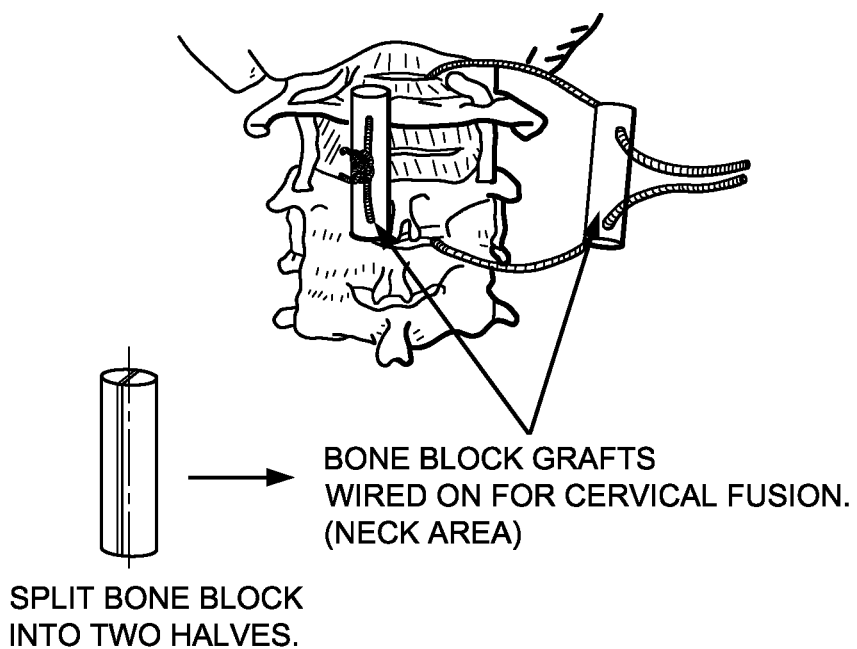
FIG. 43 shows sectioning/splitting of a bone harvested by the device of FIG. 1 for bone grafting for cervical fusion (neck area)
Figure 44:
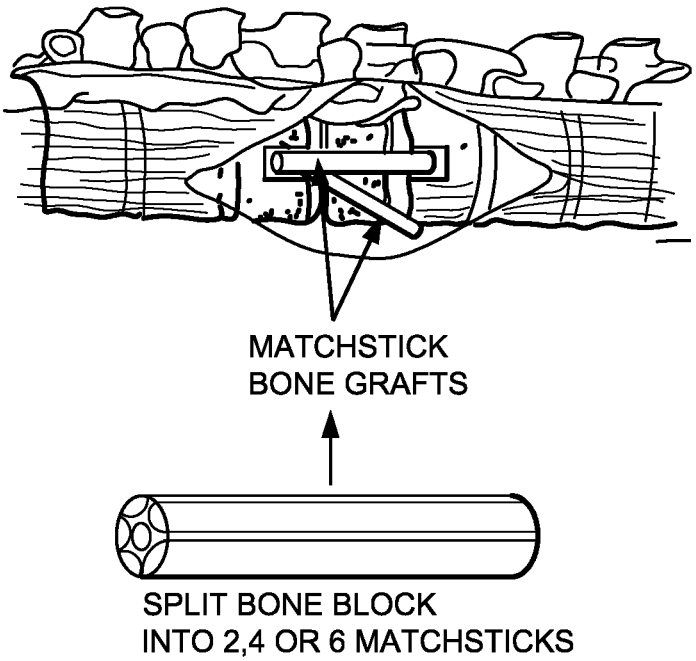
FIG. 44 shows sectioning/splitting of a bone harvested by the device of FIG. 1 into "matchstick" shaped portions for use in matchstick bone grafts.

In the human body, the largest bone is the hip bone, which includes the iliac crest. In particular, the posterior iliac crest area is the most suitable area in case a large volume of bone is required. Bone blocks harvested from this region can be used for all parts of the body. An example is given in FIG. 43, which shows use of harvested bone blocks in the cervical spine (neck region). A cylindrical bone block harvested from the hips by the use of this invention can be sectioned into two halves to graft this area. The bone can be further sectioned into matchstick shape for matchstick bone grafting anywhere along the spine, as shown in FIG. 44, and for the full range of uses for matchstick grafting in orthopaedics.

Typically, matchstick bone grafts are harvested from a rib, through openly invasive surgery, which often results in long scar(s) across the front of the torso. This invention, by its conservative harvesting of such grafts from the hips, can avoid subjecting the patient to the conventional invasive procedure. By harvesting the bone nearer to the outer border (cortical plate) of the hips, hard cortical bone (as opposed to softer cancellous bone deeper within) can equally be obtained.

The present invention aims to remove only the predetermined cylindrical block of bone within the drill cavity 38, 138, 238 of the drill body 36, 136, 236 piecemeal, and within the cortical plates of the jawbone. The advantage of this procedure, apart from its safety and simplicity, is that it allows both the inner and outer cortical plates of bone on either side of the empty socket created to be completely preserved, unlike the current methods. The socket will completely regenerate new bone after three months. This is generally referred to as socket bone.

Alternatively, a suitably sized dental implant can conveniently and immediately be placed right into this very socket. Matching sized dental implants can be chosen for press-fitting, or to be gently tapped, exactly into the neatly-cut and well-defined sockets created by the device 10, 100, 200.

It can thus be seen that:
1. the device 10, 100, 200 of this invention is quick and easy to use for any implant dentist, and is an invaluable tool for the specialist surgeons;
2. no additional risk is involved, and the device 10, 100, 200 harvests bone conservatively, methodically and precisely;
3. the bone donor site is not simply amputated. It is carved into a neat socket form, a form which is capable of fully regenerating new bone to its brim and will reappear intact after three months of healing;
4. the device 10, 100, 200 creates an intact block of bone which may be readily delivered;
5. the device 10, 100, 200 is a precision instrument which reduces extensive drilling and trauma to the patient;
6. this invention simplifies implant dentistry, and once with blocks of bone readily harvested, the invention opens many new bone grafting possibilities and encourages block bone grafting for implant dentistry. Block bone grafting can be used for all purposes of bone grafting in the jaws, including sinus grafting;
7. this invention preserves both the outer and inner cortical plates of the jawbone, leaving no permanent disfigurements;
8. in orthopaedics, the method the device 10, 100, 200 allows for harvesting the bone block from the hips is conservative, atraumatic and far less invasive. It can reduce the associated morbidity including pain and swellings related to the currently used prior art methods for this purpose;
9. only a short line incision, as equal to the inner diameter of this drill body 36, 136, 236 is required for access to any donor site. Direct vision into the site during the bone drilling and harvesting is not mandatory. This contributes greatly to an overall minimizing of the surgical wound to be sufficient for the cause.

A further usage of the device 10, 100, 200 of this invention is the harvesting of bone in orthopaedic surgery. Bone blocks can be harvested from the pelvis, iliac crest, ribs, or any suitable part of the body skeleton with the use of the device 10, 100, 200 and the bone blocks can be used in various procedures of bone grafting, including the grafting of the jaws for dental reconstruction. Another common use of bone grafts is for a procedure in orthopaedic surgery known as spinal fusion, as shown in FIGS. 29A and 29B. Other potential uses of this invention may include obtaining a bone biopsy of any part of the human skeleton, in which case the whole device containing the bone specimen is wrapped and sent to the laboratory for analysis, or for the removal of any offending object lodged in the bone, such as a gun-shot bullet. Once again, it is drilled out, wrapped and sent to the crime laboratory. More uses may include veterinary orthopaedics, pathologists, and archeological ancient bone sampling.

As like any convention trephine drill, the device 10, 100, 200 may also be used for removing failing dental implants or extracting single-rooted roots of anterior teeth (especially canines) which have become completely fused, i.e. became ankylosed to the jawbone through a process called hypercementosis.

Apart from medical uses, this invention is also capable of other industrial uses if modified up in scale, e.g. for the drilling of wood in carpentry, or of all other solid materials during manufacturing. Due to the precise nature of this device, it offers the benefit of reducing material wastage, if for example, multiple cylindrical shaped items are needed to be cut out from large bulks of a raw material.

It can be seen that the present invention offers the following advantages over prior art:
(i) With the use of the device 10, 100, 200, only a single incision equaling to the width of a tooth at the top of the gums is required for obtaining a block of bone.
(ii) The necessity for suturing the gums after the dental operation is only optional and not mandatory.
(iii) This invention removes bone in such a way that it leaves the socket it created completely capable of full bone regeneration after three months post-operative, leaving no disfigurement to the jaws.
(iv) This invention enables re-harvesting of the same socket bone repeatedly, at three-month intervals, without disfiguring the jaws, thus offering an unlimited supply of autogenous bone for use by the dental surgeon. By creating intact sockets in the jaws, it allows bone to regenerate. At the same time these sockets are of suitable shape and sizes to receive dental implants.
(v) This invention introduces a methodical and precise method over prior art for the harvesting of bone, and secures the block of bone fully contained within its body for delivery.
(vi) This invention produces blocks of autogenous bone, in identical cylindrical shapes, from one site of the jaws for another, and can be used for grafting at any part of the body skeleton, including harvesting bone from the hips for grafting the spine, such as for spinal fusion. This transportation of bone from one site to another is known as autografting.
(vii) This invention provides automation. At a factory-set depth level into the jawbone, the actuation ring 12, 112 is automatically disengaged when its outer rim impacts the top of the bone ridge and this spring-loaded ring 12, 112 begins to rotate, initiating the sawing action of the saw 30, 130, 230 whilst the drill body 36, 136, 236 rotates. The actuation ring 12, 112 serves to limit deeper penetration of the drill body 36, 136, 236 into the bone.
(viii) This invention provides an ideal method of sinus grafting for the dentist, as an alternative to the complex and invasive sinus lift procedure which requires specialists. This invention facilitates autogenous bone block grafting, as opposed to non-autogenous particulate grafting in the prior art method. The invention bypasses the failures associated with perforation of the sinus membrane. The invention also, in this way, provides an effective method for repairing oro-antral fistulas.
(ix) With the use of this invention, bone harvesting can be simpler, less invasive, involves lower risks of complications and morbidity, incurs smaller scars, and due to the usage of autogenous bone which this invention provides, achieves the final result in the shortest time frame, as autogenous bone will achieve fusion with the native bone significantly faster (three months) than all commercial non-autogenous bone (seven to twelve months), at all body recipient sites, including the jaws and the spine. All the associated advantages of using autogenous bone grafting will also be included with the use of the invention.
(x) This invention introduces a systematic method of bone grafting, whereby the congruous fitting of cylindrical shaped bone blocks into prepared holes can be applied to all areas of the jaws and the body skeleton, omitting the need for bone screws and bone pins.
(xi) Autogenous bone harvesting with this invention is quick. It saves time at the operation room, and because autogenous bone achieves all final fusion expediently, it saves overall time for all parties.

A fifth significance of this invention is that it is conservative; firstly of bone, because of the precision that it offers, carving out only exactly as required; and secondly of soft tissues, because only a line incision equal to the diameter size of the drill of this invention for it to pass through the latter and be introduced into the bone, for a minimal access.

A sixth significance of this invention is its user-friendliness, as no extra skills are required of any operator, including general dentists who are already proficient to drill bone for their surgical proceedures.

As the invention essentially does all the work on behalf of the operator, with only the need for a straight down-and-up motion within the inner and outer border limits of the bone, in-and-out of the bone, and the depth is limited by the actuation ring 12, 112, the whole process can be carried out by the operator without direct vision, but chiefly by his correct orientation and control of the device 10, 100, 200 in action, and confined only to a single direction during the entire procedure. This will eliminate the need for large surgical incisions and wide open surgery for obtaining good access and direct vision, as required with prior art tools.

Operation of the device 10, 100, 200 can be performed by tactile feel and experience, yet equally capable of harvesting sizeable blocks of autogenous bone merely through a minimal opening of the soft tissues, and similarly so into the bone. This minimal opening is feasible because the invention creates and delivers the block of bone from one end of it, limited by its diameter, but irrespective of its length. In consequence, a long harvest can result in a well-bargained minimal scar at the side of the torso which is not obvious from a front view.

This invention will greatly contribute to a smaller surgical opening of the soft tissues, which reduces the risks of damage to major nerves, such as the ilioinguinal and clunial nerves. This leads to a smaller wound and less scaring afterwards, reduces all associated discomforts and morbidity, and reduces bone and soft tissue bleedings, and thus reduces the complications of minor and deep haematoma formations, the former being common but the latter requiring surgical intervention. This invention also reduces the risk of seroma formations, i.e. pockets of fluids.

A further beneficial outcome of the use of this invention is that all the created sockets, whether in the jawbone or in the iliac crest bone, will completely heal and enjoy full bone regeneration in due course, leaving neither permanent voids nor disfigurements at the donor sites. The depth of the socket has no influence whatsoever on the time taken for the complete bone regeneration, and all depths will equally enjoy the standard bone healing time frame of three months for refillment. The overlying skin and soft tissues will heal with primary intention, as a mere fine line scar of a length equal only to the diameter of the selected drill size, of this invention device, typically approximating to an inch. The invention provides for the least invasive, simplest and precise intricate method for harvesting cylindrical blocks of autogenous bone for autografting; with the form, format and material ideal for the said purpose. Living blood vessels are also included in the autograft, which is even more ideal. The invention also increases the previously limited possibility of obtaining sufficient amount of bone material from the patient for both dental and orthopaedic purposes before resorting to the use of commercial, non-autogenous bone products.

Replicas of bone can never supersede the patient's own natural and autografting remains to be the most preferred. However, the current difficulty lies in its attainment. The present invention provides for the precision required to overcome this problem, and to compliment the intricate care and exact science of dentistry and orthopaedics. The invention allows breakthrough surgical solutions to the repair of oroantral fistulas and maxillary sinus grafting in dentistry, and provides for breakthrough in harvesting of bone from all parts of the body skeleton, including from the hips, for all various orthopaedic procedural purposes, with respect to its least invasive and atraumatic method, for equal given bone block.

The iliac crest has always been a favored donor site because of its accessibility and the large quantity of bone available. Within the ilium, grafts may be harvested from either its anterior or posterior crest.

The anterior ilium provides and adequate volume of bone for many maxillofacial and dental reconstructive procedures requiring grafting. When a larger volume of bone is required, the posterior iliac crest should be considered. However, a major disadvantage of the posterior approach is the need to turn the patient intra-operatively from the prone to the supine position, increasing the risks of injury to the patient during the change of operating position. Utilizing the anterior ilium allows the graft harvest to be performed simultaneously with the preparation of the recipient (transplanting) site. Thus, there is an advantage in developing a method for obtaining abundance of bone from the anterior ilium, which is far less invasive.

The current trend in most surgical specialties is the development of minimally invasive techniques, which are designed to minimize post-operative morbidity. Traditionally, corticocancellous blocks of autogenous bone harvested from the iliac crest using an open approach requires significant dissection of the muscle and soft tissues, resulting in complications of gait disturbance, post surgical pain, excessive blood loss, haematoma, delayed ambulation, increased length of hospital stay and paraesthesia.

The philosophy of minimally invasive surgery can be extended to the procurement of autogenous bone by means of a trephine drill. In the past trephines have been used to harvest bone biopsy specimens. While the safety and yield of trephines have been reported with respect to their use as a biopsy tool, their use in procuring bone grafts has not been thoroughly evaluated. The safety and benefit of trephines has been demonstrated by Kreibich who showed that the percutaneous sampling of bone when compared to open procedures resulted in significantly reduced pain, less pain on walking, less sensory disturbance and less local tenderness (Kreibich et al. 1994). Evaluation of the safety of biopsy trephines has shown a low incidence of complications. Trephines have a long history of application in bone biopsy harvesting for the diagnosis of metabolic bone diseases and for research purposes. These biopsy techniques demand proper sampling without destruction of bone, thereby producing viable bone for grafting purposes.

A number of researchers have evaluated the post-operativemorbidity associated with the use of trephines. Assessment in terms of post-operative pain, deep or superficial infection, and patient satisfaction revealed that the morbidity rate was extremely low, leaves minimal scaring and produces less dysesthesia than open procedures. The key factor for this result is mainly attributed to the fact that bone procurement using a trephine can proceed without muscle reflection, in contrast to traditional open procedures. It should be noted that it is the surgical practice of large incisions and extensive muscle reflections and retractions that cause morbidities and intra-operative and post-operative complications.

Unfortunately the quantity of the bone volume obtained with current trephines remains to be low, as they are at best capable of removing iliac bone of only 7.5 mm in diameter. The device 10, 200, 200 of the present invention can be scaled up for harvesting bone blocks of diameter and volumes of twice, three times or more than capably procured by the current trephines, encapsulating it and procuring it, and the diameter of which is then limited only by the dimensions of the donor site, and the iliac bone is very large. With this capability, such volume bone grafts cores so obtained may be used in providing suitable whole bone replacements for missing extremities of limbs, as in missing fingers and toes (phalanges).

With studies reporting incidences of pain, local haematomas and neuropathies following iliac crest biopsies, scientists believe that such incidences were merely attributed to a likelihood of increase in complications when heavy pressure is applied, rather than gently allowing the trephine instrument to do its work. Compared to the complications published with respect to open, invasive iliac crest grafting, the trephine technique is indeed both most simple and attractive to harvest iliac bone with significantly reduced donor site morbidity; and thus the invention aims primarily to fulfill this very purpose.

A recent study conducted in Finland which has spanned over eleven years revealed that the use of a power-driven trephine for harvesting bone from the anterior iliac crest in a minimally invasive surgical technique resulted in a record low complication rate of 0.3% and a record high patient satisfaction rate of 98.8%.

It should be understood that the above only illustrates examples whereby the present invention may be carried out, and that various modifications and/or alterations may be made thereto without departing from the spirit of invention.

It should also be understood that certain features of the invention, which are, for clarity, described in the context of separate embodiments, may be provided in combination in a single embodiment. Conversely, various features of the invention which are, for brevity, described in the context of a single embodiment, may also be provided separately or in any appropriate sub-combinations.

The invention claimed is:

1. A bone harvesting device including:
a drill for drilling into bone, said drill being a cylinder having a forward edge at an end thereof, the drill being rotatable about its longitudinal axis, for making a longitudinal circular cut into the bone for forming a cylindrical drilled bone portion as the drill is advanced into the bone, the drill having a cavity for receiving the drilled bone portion therein, the cavity having an opening at the forward end of the drill through which the cylindrical drilled bone portion passes into the cavity,
a cutter disposed in proximity to the opening which is pivotable relative to said drill about a pivoting axis which is substantially parallel to said longitudinal axis of said drill
wherein said cutter is pivotable relative to said drill between a first position in which said cutter is clear of said opening to permit the drilled bone portion to pass through the opening into the cavity and a second position in which said cutter blocks at least part of said opening to hold the drilled bone portion in the cavity, and
wherein, during movement of said cutter between said first position and said second position, said cutter moves across a plane which is substantially perpendicular to said pivoting axis, thereby cutting through and detaching the drilled bone portion from the bone, for removal with the drill.

2. A device according to claim 1 wherein said pivoting axis is fixed relative to said drill.

3. A device according to claim 1 further including an actuator for moving said cutter between the first position and the second position.

4. A device according to claim 3 wherein said actuator is movable relative to said drill between a first locking position and a second locking position, wherein when said actuator is in said first locking position, said cutter is in said first position and relative movement between said cutter and said drill is prevented, and wherein when said actuator is in said second locking position, said cutter is in said second position and relative movement between said cutter and said drill is prevented.

5. A device according to claim 4 wherein said actuator is rotatable relative to said drill about said longitudinal axis of said drill between said first locking position and said second locking position.

6. A device according to claim 4 wherein, during movement of said actuator relative to said drill from said first locking position to said second locking position, said cutter is adapted to move from said first position to said second position.

7. A device according to claim 4 wherein said actuator is movable relative to said drill between either of said first and second locking positions and an unlocked position in which movement of said actuator between said first and second locking positions is allowed.

8. A device according to claim 7 wherein said actuator is movable relative to said drill axially between either of said locking positions and said unlocked position.

9. A device according to claim 7 further including at least one spring for biasing said actuator towards either of said locking positions.

10. A device according to claim 9 wherein said actuator is connected with said drill via the at least one spring.

11. A device according to claim 1 wherein said cutter is fixedly engaged with a gear member for simultaneous rotational movement about said pivoting axis, wherein said gear member is in mesh with teeth of said actuator, and wherein upon rotation of said actuator about said longitudinal axis of said drill, said gear member is adapted to rotate relative to said drill about said pivoting axis.

12. A device according to claim 1 wherein said cavity of said drill is adapted to receive a block of bone harvested by said device.

13. A device according to claim 1 wherein said cutter includes at least one saw member.

14. A device according to claim 13 wherein said cutter includes a plurality of saw members.

15. A device according to claim 1 further comprising a bone biasing spring for biasing a block of bone received within said cavity away from said cavity.

16. A device according to claim 15 wherein said bone biasing spring extends at least in part into said cavity.

* * * * *